United States Patent [19]

Fujita et al.

[11] 4,268,624
[45] May 19, 1981

[54] PHOTOGRAPHIC LIGHT-SENSITIVE SHEET FOR THE COLOR DIFFUSION TRANSFER PROCESS

[75] Inventors: Shinsaku Fujita; Tooru Harada; Yoshinobu Yoshida, all of Minami-ashigara, Japan

[73] Assignee: Fuji Photo Film Co., Ltd., Minami-ashigara, Japan

[21] Appl. No.: 956,698

[22] Filed: Nov. 1, 1978

[30] Foreign Application Priority Data

Nov. 1, 1977 [JP] Japan .................................. 52-131278

[51] Int. Cl.³ .......................... G03C 1/40; G03C 1/10
[52] U.S. Cl. ..................................... 430/562; 430/223; 260/196; 260/198; 260/199; 260/200
[58] Field of Search ................. 96/77, 73, 99, 3, 29 D; 260/196, 198, 199, 200; 430/223, 562

[56] References Cited

U.S. PATENT DOCUMENTS

| | | | |
|---|---|---|---|
| 3,467,522 | 9/1969 | Freytag et al. | 96/99 |
| 3,954,476 | 5/1976 | Krutak et al. | 96/99 |
| 4,055,428 | 10/1977 | Koyama et al. | 96/77 |
| 4,061,496 | 12/1977 | Hannie | 96/77 |

Primary Examiner—Won H. Louie, Jr.
Attorney, Agent, or Firm—Sughrue, Rothwell, Mion, Zinn and Macpeak

[57] ABSTRACT

A photographic light-sensitive sheet for the color diffusion transfer process which comprises a support having thereon at least one light-sensitive silver halide emulsion layer having associated therewith a dye image providing material represented by the following general formula:

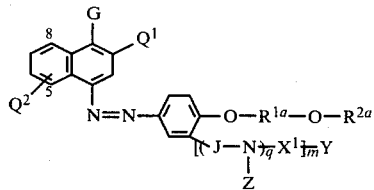

wherein $Q^1$ represents a hydrogen atom, a halogen atom, a sulfamoyl group represented by the formula $-SO_2NR^3R^4$ wherein $R^3$ represents a hydrogen atom or an alkyl group; $R^4$ represents a hydrogen atom or an alkyl group, an aralkyl group or an aryl group; and $R^3$ and $R^4$ may combine directly or through an oxygen atom to form a ring; a group represented by the formula $-SO_2R^5$ wherein $R^5$ represents an alkyl group or a benzyl group; a carboxy group, a group represented by the formula $-COOR^6$ wherein $R^6$ represents an alkyl group, a phenyl group or a substituted phenyl group or a group represented by the formula $-CONR^3R^4$ wherein $R^3$ and $R^4$ each has the same meaning as defined above; $Q^2$ is positioned at the 5- or the 8-position to the hydroxy group and represents a hydroxy group, a group represented by the formula $-NHCOR^{4a}$ or a group represented by the formula $-NHSO_2R^{4a}$ wherein $R^{4a}$ has the same meaning as $R^4$ defined above, except for the absence of a hydrogen atom; $R^{1a}$ represents an alkylene group having 2 or more carbon atoms; $R^{2a}$ represents an alkyl group; Y represents a moiety which releases or provides, as a result of development processing under alkaline conditions, an azo dye having a different diffusibility from that of said dye image-providing material; m is 0 or 1; q is 0 or 1; J represents a divalent group selected from a sulfonyl group and a carbonyl group; Z represents a hydrogen atom, an alkyl group or a substituted alkyl group; $X^1$ represents a divalent bonding group represented by the formula $-A_1-(L)_n-(A_2)_p-$ wherein $A_1$ and $A_2$ are the same or different and each represents an alkylene group or an arylene group; L represents a divalent group selected from an oxy group, a carbonyl group, a carboxyamido group, a carbamoyl group, a sulfonamido group, a sulfamoyl group, a sulfinyl group and a sulfonyl group, and n and p each represents 0 or 1; and G represents a hydroxyl group, a salt thereof, or a hydrolyzable acyloxy group represented by the formula

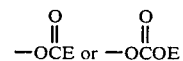

wherein E represents an alkyl group, a substituted alkyl group or an aryl group. The compound is a dye image providing material which provides a magenta dye image having superior properties.

15 Claims, No Drawings

PHOTOGRAPHIC LIGHT-SENSITIVE SHEET FOR THE COLOR DIFFUSION TRANSFER PROCESS

BACKGROUND OF THE INVENTION

1. Field of the Invention

The present invention relates to a photographic light-sensitive sheet for the color diffusion transfer process and, more particularly, to a silver halide photographic light-sensitive sheet for the color diffusion transfer process containing a dye image providing material having a novel redox moiety.

2. Description of the Prior Art

Color diffusion transfer color image forming processes using a dye releasing redox compound are described in Japanese patent application (OPI) No. 104343/1976 (The term "OPI" as used herein refers to a "published unexamined Japanese patent application"), U.S. Pat. 3,932,381, 3,942,987, 3,928,312, 3,931,144, 3,954,476 and Research Disclosure, No. 13024 (1957). The term "dye releasing redox compound" means a compound containing therein a group referred to as a redox moiety and a dye or a dye precursor moiety. The redox moiety renders the redox compound immobile due to a ballast group attached thereto, but under alkaline conditions the compound splits and releases a compound having the dye oiety (a dye compound). For instance, when a light-sensitive element having a light-sensitive silver halide emulsion layer and a dye-releasing redox compound associated therewith is exposed and developed with an alkaline processing solution, the redox moiety per se is oxidized in proportion to the amount of developed silver halide and the compound splits into a compound having a dye moiety and a non-diffusible quinone compound. As a result, the compound having a dye moiety diffuses into an image-receiving layer to provide a transferred image therein.

Examples of dye-releasing redox compounds which release magenta dyes are described in U.S. Pat. No. 3,932,380 and 3,931,144, etc. However, technical problems are encountered, using these magenta dye releasing redox compounds specifically described in such prior art, in that the transferred images have insufficient stability. For example, the light fastness of the images is not adequate and the images fade to a large extent even in a dark place. Also, the transfer of the dye compound is not adequate.

For instance, with respect to the fading-in-dark of transferred dye images, it has been known that unreacted monomer (such as acrylic acid, butyl acrylate, etc.) in the neutralizing layer containing a polymer acid such as poly-acrylic acid, a copolymer of acrylic acid and butyl acrylate, etc., as disclosed in U.S. Pat. No. 3,362,819 hereinafter described, adversely influences to the fading of transferred dye images. It has also been found upon further investigation that unreacted butyl acrylate monomer exceptionally degrades magenta dye images obtained from prior art dye-releasing redox compounds such as described in U.S. Pat. No. 3,932,380. However, it is extremely difficult from a technical standpoint to limit the amount of unreacted monomer during the synthesis of polymer acid for a neutralizing layer to an extent that it does not adversely influence the light fastness of the images. Therefore, it has been desired to develop a redox compound which releases a dye compound which is less sensitive to such a monomer.

Furthermore, it has also been found upon further investigation that using these prior art dye-releasing redox compounds discussed above, the visual spectrum of the transferred image is too wide to affect good color reproduction.

SUMMARY OF THE INVENTION

A first object of the present invention is to provide a dye image providing material which provides a stable magenta dye image.

A second object of the present invention is to provide a dye image providing material having a dye moiety whose color hue is excellent.

A third object of the present invention is to provide a dye image providing material which provides a transferred dye image which does not change hue with pH.

A fourth object of the present invention is to provide a photographic light-sensitive sheet for the color diffusion transfer process containing a dye image providing material which provides a transferred magenta dye image having a sufficiently high optical density in the presence of a relatively small amount of silver halide.

A fifth object of the present invention is to provide a so-called "negative utilizable" photographic light-sensitive sheet for the color diffusion transfer process in which a light-sensitive element is also utilized.

A sixth object of the present invention is to provide an intermediate of such a dye image-providing material.

The inventors have conducted various investigations and found that the above-described objects are effectively attained by a photographic light-sensitive sheet with satisfactory photographic properties for the color diffusion transfer process which contains a dye image providing material represented by the following general formula:

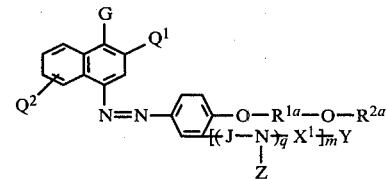

and preferably by the following formulae (I) and (II):

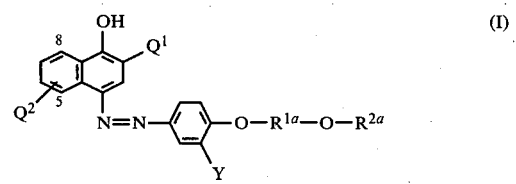

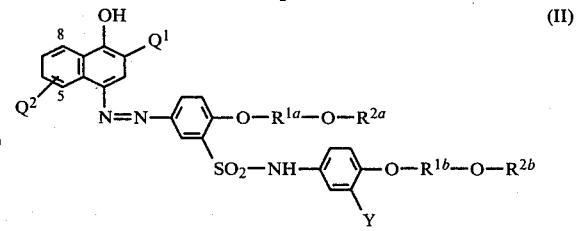

wherein $Q^1$ represents a hydrogen atom, a halogen atom, a sulfamoyl group represented by the formula $-SO_2NR^3R^4$ wherein $R^3$ represents a hydrogen atom, an alkyl group including a substituted and unsubstituted alkyl groups; $R^4$ represents a hydrogen atom, an alkyl group, including substituted and unsubstituted alkyl groups, an aralkyl group or an aryl group; and $R^3$ and $R^4$ may combine directly or through an oxygen atom to form a ring; a group represented by the formula —SO$_2$R$^5$ wherein $R^5$ represents an alkyl group, including substituted and unsubstituted alkyl groups or a benzyl group; a carboxy group, a group represented by the formula —COOR$^6$ wherein $R^6$ represents an alkyl group, including substituted and unsubstituted alkyl groups, a phenyl group or a substituted phenyl group; or a group represented by the formula —CONR$^3$R$^4$ wherein $R^3$ and $R^4$ each has the same meaning as defined above; $Q^2$ is positioned at the 5- or the 8-position to the hydroxy group and represents a hydroxy group, a group represented by the formula —NHCOR$^{4a}$ or a group represented by the formula —NHSO$_2$R$^{4a}$ wherein $R^{4a}$ has the same meaning as $R^4$ defined above, except for the absence of a hydrogen atom; m is 0 or 1; q is 0 or 1; J represents a divalent group selected from a sulfonyl group and a carbonyl group; Z represents a hydrogen atom or an alkyl group, including substituted and unsubstituted alkyl groups; $X^1$ represents a divalent bonding group represented by the formula —A$_1$—(L-)$_n$—(A$_2$)$_p$—wherein A$_1$ and A$_2$ are the same or different and each represents an alkylene group or an arylene group; L represents a divalent group selected from an oxy group, a carbonyl group, a carboxy-amido group, a carbamoyl group, a sulfonamido group, a sulfamoyl group, a sulfinyl group and a sulfonyl group; and n and p each represents 0 or 1; G represents a hydroxyl group, a salt thereof, or a hydrolyzable acyloxy group

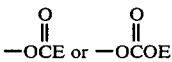

represented by the formula

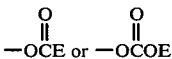

wherein E represents an alkyl group including substituted and unsubstituted alkyl groups or an aryl group; $R^{1a}$ and $R^{1b}$, which may be the same or differnet, each represents an alkylene group having 2 or more, preferably 2 to 8, carbon atoms; $R^{2a}$ and $R^{2b}$, which may be the same or different, each represents an alkyl group including unsubstituted as well as substituted alkyl groups; and Y represents a moiety which releases or provides, as a result of development processing under alkaline conditions, an azo dye having a different diffusibility from that of said dye image-providing material.

DETAILED DESCRIPTION OF THE INVENTION

In the description hereinafter, the terms $R^1$ and $R^2$ refer to $R^{1a}$ and $R^{1b}$ and $R^{2a}$ and $R^{2b}$, respectively, unless otherwise indicated.

In the above-described general formulas, the compound is characterized by the presence of the —O—R$^1$—O—R$^2$ group in the dye moiety, more particularly the moiety corresponding to the diazo component. The —O—R$^{1a}$—O—R$^{2a}$ group positioned at the 4-position to the azo group and the -SO$_2$NH- group (Y in the formula (I)) positioned at the 3-position is another characteristic. In particular, in the compound represented by the formula (I), it is important that the —O—R$^{1a}$—O—R$^{2a}$ group and Y be positioned ortho to each other. It is belived that due to this structural feature, the function of Y as a redox moiety is intensified and, thus, the dye compound is effectively released from the dye-releasing redox compound resulting in improved transferability. In fact, improved transferability (particularly improved transferability at a low pH) is not observed where the relative position of these two groups is different from that of the present invention. For example, where the —O—R$^{1a}$—O—R$^{2a}$ group is positioned at the 2-position with respect to the azo group and Y is positioned at the 5-position with respect to the azo group, improved transferability is not obtained.

Likewise, the presence of the —O—R$^{1b}$ —O—R$^{2b}$ group and Y ortho to each other is important in the compound represented by the formula (II). Due to this fact, the effect that the hue of a transferred image from the compound of the formula (II) does not change with a change in pH. Although there are various hypotheses for such improvement, one reason is the presence of an intramolecular hydrogen bond as shown in formula below which suppresses dissociation of —SO$_2$NH.

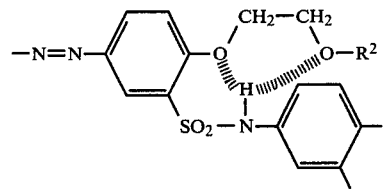

In fact, it has been found that the hue of the transferred image changes with a change in pH, where the relative position of these two groups is different than that of the present invention, for example, when the —O—R$^{1a}$—O—R$^{2a}$ group is positioned at the 2-position to the azo group and Y is positioned at the 5-position to the azo group, even though the —O—R$^{1a}$—O—R$^{2a}$ is present.

It is also recognized that a visual spectrum of a transferred image formed from the compound of the present invention is sharp which exerts a favorable influence on the color reproduction.

The alkylene group having 2 or more carbon atoms represented by $R^1$ can be a straight chain or branched chain alkylene group and an alkylene group having 2 or 4 carbon atoms is preferred. Although $R^1$ can be a branched chain alkylene group, a branched chain alkylene group which forms an acetal linkage, i.e., a —O—C—O—R$^2$ linkage, is exluded. Particularly preferred examples of $R^1$ are a straight chain alkylene group represented by the formula —(CH$_2$)$_p$—, wherein p is an integer of 2 to 4, and a branched chain alkylene group having 3 to 4 carbon atoms such as —CH(CH$_3$)CH$_2$— and —CH$_2$CH$_2$CH(CH$_3$)— with an alkylene group which forms an acetal linkage being excluded as described above. In view of easy availability of starting materials to produce the dye image providing material of this invention, a —CH$_2$CH$_2$— group is particularly advantageous for $R^1$. When $R^1$ represents a methylene group, an acetal linkage, in this case a —O—CH$_2$—O—R$^2$ linkage, is formed, which is undesirable since it is chemically unstable, particularly under acidic conditions, and tends to decompose during the preparation thereof. For the same reason, groups where two oxygen atoms are bonded to the same carbon atom in the —O—R$^1$—O—R$^2$ group (i.e., forming an acetal linkage), are also not desirable. The alkyl group represented by $R^2$ can be an unsubstituted or substituted straight chain or branched chain alkyl group and preferably is an alkyl group having 1 to 8 carbon atoms. From the standpoint of the preparation of the compounds of this invention, an unsubstituted alkyl group is preferred. A particularly preferred example of $R^2$ is a straight chain or branched chain alkyl group having 1 to 4 carbon atoms (for example, a methyl group, an ethyl group, an n-propyl group, an isopropyl group, an n-butyl group, etc.). Suitable substituents which can be present on the alkyl group for $R^2$ include, for example, an alkoxy group (for example, a methoxy group, an ethoxy group, etc.), a dialkylamino group (for example, a diethylamino group, etc.), and the like.

In the sulfamoyl group represented by the formula $-SO_2NR^3R^4$ for $Q^1$, $R^3$ is preferably a hydrogen atom, an alkyl group having 1 to 8 carbon atoms (more preferably 1 to 4 carbon atoms). The alkyl group may be a substituted alkyl group wherein there are 1 to 8 carbon atoms (more preferably 1 to 4 carbon atoms) in the alkyl moiety. $R^4$ is preferably a hydrogen atom, an alkyl group 1 to 8 carbon atoms (more preferably 1 to 4 carbon atoms) including a straight chain, branched chain or cyclic alkyl group, and substituted alkyl groups having 1 to 8 carbon atoms (more preferably 1 to 4 carbon atoms) in the alkyl moiety, an unsubstituted benzyl group, a substituted benzyl group having 7 to 12 carbon atoms, an unsubstituted phenyl group, or a substituted phenyl group having 6 to 9 carbon atoms. Also, $R^3$ and $R^4$ may be combined directly or through an oxygen atom to form a 5-or 6-membered ring. The cases where: (1) $R^3$ and $R^4$ each represents a hydrogen atom and (2) one of $R^3$ and $R^4$ represents a hydrogen atom and the other of $R^3$ and $R^4$ represents an alkyl group having 1 to 4 carbon atoms, are particularly preferred because of easy availability of the starting materials and excellent transferability of the dye compound formed. The same is true for the $-CONR^3R^4$ group. That is, $R^3$ and $R^4$ are preferably both hydrogen or one is hydrogen and the other $C_1-C_4$ alkyl.

With respect to the $-SO_2R^5$ group, $R^5$ preferably represents an alkyl group or a benzyl group. The alkyl may be an unsbustituted having 1 to 8 carbon atoms, or substituted having 1 to 8 carbon atoms in the alkyl moiety. In particular, an alkyl group having 1 to 4 carbon atoms and a benzyl group are preferred because of easy availiability of the starting materials and excellent transferability of the dye compound formed. In case of the $-COOR^6$ group, $R^6$ preferably represents an alkyl group, an unsubstituted phenyl group or a substituted phenyl group having 6 to 9 carbon atoms. The alkyl may be substituted or unsubstituted having 1 to 8 carbon atoms (more preferably 1 to 4 carbon atoms) in the alkyl moiety.

Examples of suitable substituents which can be present in the above-described substituted alkyl groups represented by $R^3$ to $R^6$ include one or more of a cyano group, an alkoxy group, a hydroxy group, a carboxy group, a sulfo group, a tetrahydrofuryl group, a furyl group, a vinyl group, etc. Further, examples of suitable substituents which can be present in the above-described substituted phenyl group represented by $R^4$ or $R^6$ include one or more of a hydroxy group, a halogen atom, a carboxy group, a sulfo group, a sulfamoyl group, an alkyl group, an alkoxy group, etc. The number of the substituents is preferably 1 or 2.

The above-described substituted benzyl group represented by $R^4$ can preferably have 1 or 2 substituents. Examples of suitable substituents include ahydroxy group, a halogen atom, a carboxy group, a sulfo group, a sulfamoyl group, an alkyl group, an alkoxy group, a methylenedioxy group, etc. In particular, a hydroxy group, an alkoxy group having 1 to 4 carbon atoms and a methylenedioxy group are preferred. Examples of the substituted benzyl groups include an o-, m- or p-hydroxybenzyl group, an o-, m- or p-methoxybenzyl group, a 3-hydroxy-4-methoxybenzyl group, a 4-hydroxy-3-methoxybenzyl group, 2-hydroxy-3-methoxybenzyl group, a 2,5-dimethoxybenzyl group, a 3,4-dimethoxybenzyl group, a methylenedioxybenzyl group, etc.

Examples of the cyclic group formed when $R^3$ and $R^4$ combine are as follows:

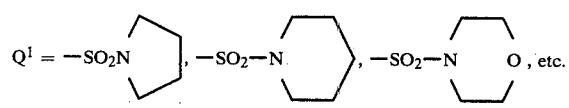

As Z, a hydrogen atom is preferable. Alkyl group represented by Z may be straight or branched and preferably contain 1 to 8 carbon atoms, particularly preferably is an alkyl group contain 1 to 4 carbon atoms (e.g., a methyl group, an ethyl group, an n-propyl group, an isopropyl group, an n- butyl group, etc.).

As the substituted alkyl group represented by Z, substituted alkyl groups wherein the alkyl moiety has 1 to 8 carbon atoms are preferable, with those having 1 to 4 carbon atoms in the alkyl moiety being particularly preferable. As the examples of the substitutents for the substituted alkyl groups, there are illustrated a cyano group, an alkoxy group, a hydroxyl group, a carboxyl group, a sulfo group, etc.

As the alkylene group represented by $A_1$ or $A_2$, those containing 1 to 8 carbon atoms, preferably 1 to 4 carbon atoms, are suitable. As the arylene group represented by $A_1$ or $A_2$, those having 6 to 10 carbon atoms are suitable. Such alkylene or arylene group may have the substituents described for the aforesaid $R^3$ or $R^4$. Above all, as the arylene group, a phenylene group substituted by the same alkoxyalkoxy group as foregoing $R^{2a}-O-R^{1a}-O-$ is preferable.

Y represents a moiety which releases or provides, as a result of development processing under alkaline conditions, an azo dye having a different diffusibility from that of the azo dye image-providing material.

As the azo dye image-providing materials, there are illustrated non-diffusible image-providing materials (azo dye-releasing redox compounds) which provide a diffusible dye as a result of self splitting due to oxidation by the development processing. Examples of Y effective for this type of compound are N-substituted sulfamoyl groups. For example, there can be illustrated as Y the group represented by the following formula (A):

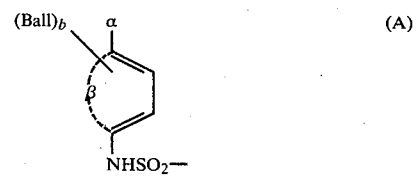

In the above formula, β represents non-metallic atoms necessary to complete a benzene ring, to which a carbon ring or a hetero ring may be fused to form, for example, a naphthalene ring, a quinoline ring, a 5,6,7,8-tetrahydronaphthalene ring, a chroman ring, etc. Further, said benzene ring or said ring wherein a carbon ring or hetero ring is fused to the benzene ring may have a substituted or substituents such as a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboalkoxy group, a hetero ring group, etc.

α represents an —OG$^1$ or —NHG$^2$ group, wherein G$^1$ represents a hydrogen atom or a group capable of forming a hydroxyl group by hydrolysis, and preferably represents a hydrogen atom,

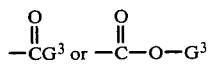

wherein G$^3$ represents an alkyl group, in particular, alkyl group having 1 to 18 carbon atoms (such as a methyl group, an ethyl group, a propyl group, etc.), a halogen-substituted alkyl group having 1 to 18 carbon atoms (such as a chloromethyl group, a trifluoromethyl group, etc.), a phenyl group or a substituted phenyl group, and G$^2$ represents a hydrogen atom, an alkyl group having 1 to 22 carbon atoms or a hydrolyzable group. Preferable examples of said hydrolyzable group represented by G$^2$ are

—SO$_2$G$^5$ or —SOG$^5$, wherein G$^4$ represents an alkyl group having 1 to 4 carbon atoms (such as a methyl group); a halogen-substituted alkyl group (such as mono-, di- or tri-chloromethyl group or a trifluoromethyl group); an alkylcarbonyl group (such as an acetyl group); an alkoxy group; a substituted phenyl group (such as a nitrophenyl group or a cyanophenyl group); a phenyloxy group unsubstituted or substituted by a lower alkyl group or a halogen atom; a carboxyl group; an alkyloxycarbonyl group; an aryloxycarbonyl group; an alkylsulfonylethoxy group; or an arylsulfonylethoxy group, and G$^5$ represents a substituted or unsubstituted alkyl or aryl group.

Further, b is an integer of 0, 1 or 2, and b represents 1 or 2, preferably 1, except when said α represents —NHG$^2$ wherein G$^2$ represents an alkyl group making the compound of the general formula (A) immobile and non-diffusible, namely, when α represents a group represented by —OG$^1$ or —NHG$^2$ wherein G$^2$ represents a hydrogen atom, an alkyl group having 1 to 8 carbon atoms or a hydrolyzable group. Ball represents a ballast group which will be described in detail hereinafter.

Specific examples of this type Y are described in U.S. Published Application B351,673, U.S. Pat. No. 3,928,312 and Japanese Patent Application (OPI) No. 50736/1978.

As the another examples of Y suitable for this type of compounds, there are illustrated the group represented by the following formula (B):

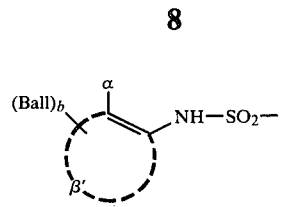

In the above formula, Ball, α and b are the same as defined in formula (A), β' represents the atoms necessary to form a carbon ring, for example, a benzene ring, to which a carbon ring or a hetero ring may further be fused to form a naphthalene ring, a quinoline ring, a 5,6,7,8-tetrahydronaphthalene ring, a chroman ring, etc. The above-described various rings may be further substituted by a halogen atom, an alkyl group, an alkoxy group, an aryl group, an aryloxy group, a nitro group, an amino group, an alkylamino group, an arylamino group, an amido group, a cyano group, an alkylmercapto group, a keto group, a carboalkoxy group, a hetero ring or the like. Specific examples of this type Y are described in U.S. Pat. Nos. 4,055,428 and 4,053,312.

As the further examples of Y suitable for this type compounds, there are illustrated the group represented by general formula (C):

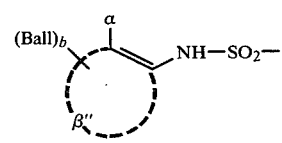

In the above formula, Ball, α and b are the same as defined in formula (A), and β" represents atoms necessary to form a hetero ring such as a pyrazole ring, a pyridine ring, etc., to which a carbon ring or a hetero ring may further be fused. The above-described rings may be substituted by the same substituents as those for the rings described in formula (B). Specific examples of this type Y are described in Japanese Patent Application (OPI) No. 104343/1976.

As still further examples of Y suitable for this type compounds, there are illustrated those represented by general formula (D):

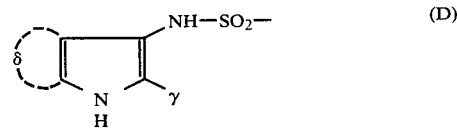

In the above formula, γ preferably represents a hydrogen atom; an alkyl group, aryl group or hetero ring group which may be unsubstituted or substituted; or —CO—G$^6$ wherein G$^6$ represents

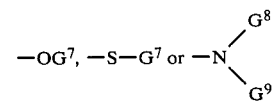

(herein G$^7$ represents a hydrogen atom, an alkyl group, a cycloalkyl group or an aryl group, which may be substituted, G$^8$ represents the same group as G$^7$ or an acyl group derived from an aliphatic or aromatic carboxylic acid or from sulfonic acid, and G$^9$ represents a hydrogen atom or a substituted or unsubstituted alkyl group), δ represents the atoms necessary for completing a fused benzene ring which ring may have one or more substituents, and γ and/or the substituents on said fused benzene ring completed by δ is a ballast group or a ballast-containing group. Specific examples of this type Y are described in Japanese Patent Application (OPI) Nos. 104343/1976 and 46730/1978.

As still further examples of Y suitable for this type compounds, there are illustrated the group represented by general formula (E):

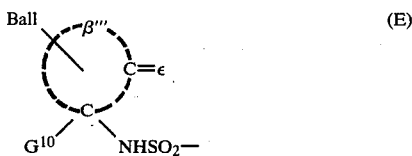

In the above formula, Ball is the same as defined in formula (A), ε represents an oxygen atom or =NG" (G" represents a hydroxyl group or an amino group which may be substituted) and, when ε represents =NG", a typical example of G" is that in =C=N—G" formed by the dehydration reaction between a carbonyl reagent of $H_2N$—G" and a ketone group. Examples of the compound of $H_2N$—G" are hydroxylamines, hydrazines, semicarbazides, thiosemicarbazides, etc. To be specific, there are illustrated, as the hydrazines, hydrazine, phenylhydrazine, substituted phenylhydrazine having in the phenyl moiety a substituent or substituents such as an alkyl group, an alkoxy group, a carboalkoxy group, a halogen atom, etc., isonicotinic acid hydrazine, etc. As the semicarbazides, there are illustrated, phenylsemicarbazide or substituted phenylsemicarbazide substituted by an alkyl group, an alkoxy group, a carboalkoxy group, a halogen atom, etc. As the semithiocarbazides, there are illustrated the same derivatives as with semicarbazides.

β''' in the formula represents a 5-, 6- or 7-membered saturated or unsaturated non-aromatic hydrocarbons. To be specific, there are illustrated, for example, cyclopentanone, cyclohexanone, cyclohexenone, cyclopentenone, cycloheptanone, cycloheptenone, etc.

These 5- to 7-membered non-aromatic hydrocarbon rings may be fused to other rings at a suitable position to form a fused ring system. As the other ring, various rings may be used regardless of whether they show aromaticity or not or whether they are hydrocarbon rings or hetero rings. However, in the case of a fused ring being formed, fused systems herein benzene and the above-described 5- to 7-membered non-aromatic hydrocarbon ring are fused to each other such as indanone, benzcyclohexenone, benzcycloheptenone, etc., are preferable in the present invention.

The above-described 5- to 7-membered non-aromatic hydrocarbon rings or the above-described fused rings may have one or more substituents such as an alkyl group, an aryl group, an alkyloxy group, an aryloxy group, an alkylcarbonyl group, an arylcarbonyl group, an alkylsulfonyl group, an arylsulfonyl group, a halogen atom, a nitro group, an amino group, an alkylamino group, an arylamino group, an amido group, an alkylamido group, an arylamido group, a cyano group, an alkylmercapto group, an alkyloxycarbonyl group, etc.

$G^{10}$ represents a hydrogen atom, or a halogen atom such as fluorine, chlorine or bromine.

Specific examples of this type Y are described in Japanese Patent Application (OPI) No. 3819/1978.

As the still further examples of Y for the compounds of the present invention, there are those described in, for example, U.S. Pat. Nos. 3,443,930, 3,443,939, 3,628,952, 3,844,785 and 3,443,943.

As the different type compounds of the dye-releasing redox compounds, there are illustrated non-diffusible dye image-providing compounds which release a diffusible dye under alkaline condition through self cyclization or the like but, when reacted with the oxidation product of developing agent, which do not substantially release the dye.

As the examples of Y effective for this type compounds, there are illustrated those represented by formula (F):

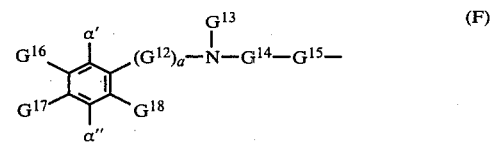

In the above formula, α' represents an oxidizable nucleophilic group such as a hydroxyl group, a primary or secondary amino group, a hydroxyamino group or a sulfonamido group, or the precursor thereof, and preferably represents a hydroxyl group.

α" represents a dialkylamino group or any of those defined for α', preferably a hydroxyl group. $G^{14}$ represents an electrophilic group such as —CO—, —CS—, etc., preferably —CO—. $G^{15}$ represents an oxygen atom, a sulfur atom, a selenium atom, a nitrogen atom, etc., and, when $G^{15}$ represents a nitrogen atom, it may be substituted by a hydrogen atom, an unsubstituted or substituted alkyl group having 1 to 10 carbon atoms, or an aromatic compound residue having 6 to 20 carbon atoms. Preferable $G^{15}$ is an oxygen atom. $G^{12}$ represents an alkylene group containing 1 to 3 carbon atoms, and a represents 0 or 1, preferably 0. $G^{13}$ is a substituted or unsubstituted alkyl group containing 1 to 40 carbon atoms or a substituted or unsubstituted aryl group containing 6 to 40 carbon atoms, preferably an alkyl group. $G^{16}$, $G^{17}$ and $G^{18}$ each represents a hydrogen atom, a halogen atom, a carbonyl group, a sulfamyl group, a sulfonamido group, an alkyloxy group containing 1 to 40 carbon atoms, or the same as defined for $G^{13}$ or, when taken together, $G^{16}$ and $G^{17}$ may form a 5- to 7-membered ring. Also, $G^{17}$ may be

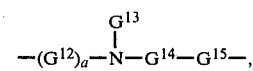

provided that at least one of $G^{13}$, $G^{16}$, $G^{17}$ and $G^{18}$ represents a ballast group.

Specific examples of this type Y are described in U.S. Pat. No. 3,980,479.

As the examples of Y suitable for this type compounds, there are further illustrated the group represented by general formula (G):

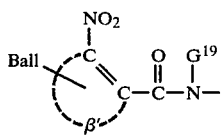

wherein Ball and β' are the same as defined in formula (B), and $G^{19}$ represents an alkyl group (including substituted alkyl group). Specific examples of this type Y are described in Japanese Patent Application (OPI) No. 35533/1978.

As the examples of Y suitable for this type compounds, there are further illustrated the group represented by general formula (H):

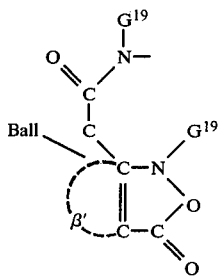

wherein Ball and β' are the same as defined in formula (B), and $G^{19}$ is the same as defined in formula (G). Specific examples of this type Y are described in U.S. Pat. No. 3,421,964 and Japanese Patent Application (OPI) No. 4819/1977.

As the different type compounds of the azo dye image-providing compounds, there are illustrated non-diffusible compounds (dye-releasing couplers) which release a diffusible dye upon coupling reaction with an oxidation product of a color developing agent oxidized by silver halide. As the examples of Y effective for such compounds, the groups described in U.S. Pat. No. 3,227,550 are typical. For example, there are illustrated as Y those represented by the following general formula (J):

(Ball-Coup)$_t$-Link-  (J)

wherein Coup represents a coupler residue capable of coupling with an oxidation product of a color developing agent, for example, a 5-pyrazolone type coupler residue, a phenol type coupler residue, a naphthol type coupler residue, an indanone type coupler residue or an open chain ketomethylene coupler residue. Ball represents a ballast group. Link represents a group bonded to an active cite of Coup moiety, which bond with Coup moiety will be split upon coupling reaction between the dye image-providing material represented by formula (I) containing the group represented by formula (J) as Y and an oxidation product of a color developing agent. Examples of the Link are an azo group, an azoxy group, —O—, —Hg—, an alkylidene group, —S—, —S—S— or —NHSO$_2$—, and t represents 1 or 2 when Link represents an alkylidene group or represents 1 when Link represents other group described above.

Of groups Y represented by formula (J), preferable groups are those wherein Coup represents a phenol type coupler residue, a naphthol type coupler residue or an indanone type coupler residue, and Link represents —NHSO$_2$—.

As the still different type compounds of the dye image-providing materials, there are illustrated the compounds (dye developing agent) which are initially diffusible under alkaline conditions but, when oxidized through development processing, become non-diffusible. Typical examples of Y effective for this type compounds are those described in U.S. Pat. No. 2,983,606.

Of the above-described compounds, particularly preferable ones are dye-releasing redox compounds and effective groups Y are N-substituted sulfamoyl groups. As the N-substituents for the N-substituted sulfamoyl groups, carbon ring groups (in particular, o- or p-hydroxyaryl group having a ballast group bonded thereto being preferable) or hetero ring groups are desirable. As the examples of N-carbon ring substituted sulfamoyl groups, those represented by formulae (A) and (B) are particularly preferable. As the examples of N-hetero ring substituted sulfamoyl groups, those represented by formulae (C) and (D) are particularly preferable. As Y, the group represented by general formula (III) are particularly preferable.

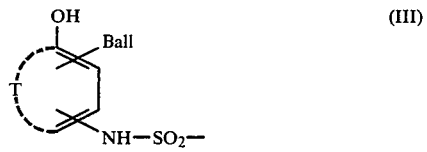

wherein Ball represents a ballast group; T represents the carbon atoms necessary to complete a benzene ring, which may be unsubstituted or substituted, or a naphthalene ring, which may be unsubstituted or substituted, the —NHSO$_2$— group is present at the o- or p-position to the hydroxy group; and when T represents the atoms necessary to complete a naphthalene ring, Ball can be bonded to either of the two rings.

Examples of suitable substituents which can be present on the benzene ring or the naphthalene ring include, for example, an alkyl group (preferably an alkyl group having 1 to 7 carbon atoms), halogen atom (such as a chlorine atom, etc.), etc.

The ballast group, Ball, is an organic ballast group capable of rendering the dye-releasing redox compound non-diffusible during development in an alkaline processing solution and preferably is or contains a hydrophobic residue having 8 to 32 carbon atoms. This organic ballast group can be bonded to the dye-releasing redox compound directly or through a linking group, for example, an imino bond, an ether bond, a thioether bond, a carbonamido bond, a sulfonamido bond, a ureido bond, an ester bond, an imido bond, a carbamoyl bond, a sulfamoyl bond, etc.

Specific examples of ballast groups are illustrated below.

An alkyl group or an alkenyl group (for example, a dodecyl group, an octadecyl group, etc.), an alkoxyalkyl group (for example, a 3-(octyloxy)propyl group, a 3-(2-ethylundecyloxy)propyl group, etc., as described in Japanese Patent Publication No. 27563/1964, etc.), an alkylaryl group (for example, a 4-nonylphenyl group, a 2,4-di-tert-butylphenyl group, etc.), an alkylaryloxyalkyl group (for example, a 2,4-di-tert-pentylphenoxymethyl group, an α-(2,4-di-tert-phenylphenoxy)propyl group, a 1-(pentadecylphenoxy)ethyl group, etc.), an acylamidoalkyl group (for example, a group described in U.S. Pat. Nos. 3,337,344 and 3,418,129, a 2-(N-butylhexadecanamido)-ethyl group, etc.), an alkoxyaryl or aryloxyaryl group (for example, a 4-(n-octadecyloxy)-phenyl group, a 4-(4-n-dodecylphenyloxy)phenyl group, etc.), a residue containing both an alkyl or alkenyl long-chain aliphatic group and a water-solubilizing group such as a carboxy group or a sulfo group (for example, a 1-carboxymethyl-2-nonadecenyl group, a 1-sulfoheptadecyl group, etc.), an alkyl group substituted with an ester group (for example, a 1-ethoxycarbonylheptadecyl group, a 2-(n-dodecyloxycarbonyl-)ethyl group, etc.), an alkyl group substituted with an aryl group or a heterocyclic group (for example, a 2-[4-(3-methoxycarbonylheneicosanamido)-phenyl]ethyl group, a 2-[4-(2-n-octadecylsuccinimido)phenyl]-ethyl group, etc.), and an aryl group substituted with an aryloxyalkoxycarbonyl group (for example, a 4-[2-(2,4-ditertpentylphenoxy)-2-methylpropyloxycarbonyl]phenyl group, etc.).

Of the above-described organic ballast groups, those bonded to a bridging group as represented by the following general formulae (IV) to (VII) are particularly preferred.

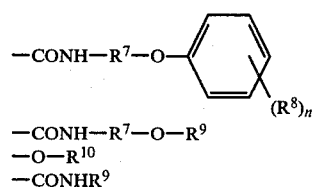
(IV)

—CONH—R⁷—O—R⁹ (V)
—O—R¹⁰ (VI)
—CONHR⁹ (VII)

wherein $R^7$ represents an alkylene group having 1 to 10 carbon atoms, preferably 1 to 6 carbon atoms (such as a propylene group, a butylene group, etc.); $R^8$ represents a hydrogen atom or an alkyl group having 1 to 10 carbon atoms, preferably 1 to 6 carbon atoms (such as a tert-amyl group, etc.); n represents an integer of 1 to 5 (preferably 1 to 2); $R^9$ represents an alkyl group having 4 to 30 carbon atoms, preferably 10 to 20 carbon atoms (such as a dodecyl group, a tetradecycl group, a hexadecyl group, etc.); and $R^{10}$ represents an alkyl group having 8 to 30 carbon atoms, preferably 10 to 20 carbon atoms (such as a hexadecyl group, an octadecyl group, etc.) or a substituted alkyl group having 8 or more carbon atoms in which the alkyl moiety has one or more carbon atoms, with examples of suitable substituents being one or more of, for example, a carbamoyl group, etc.

Specific exmples of the sulfamoyl groups represented by the formula (III) are illustrated below:

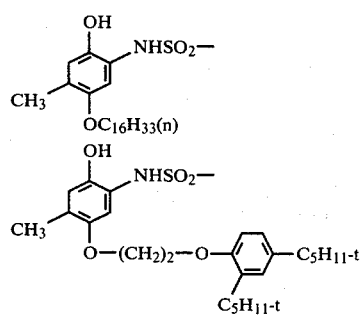

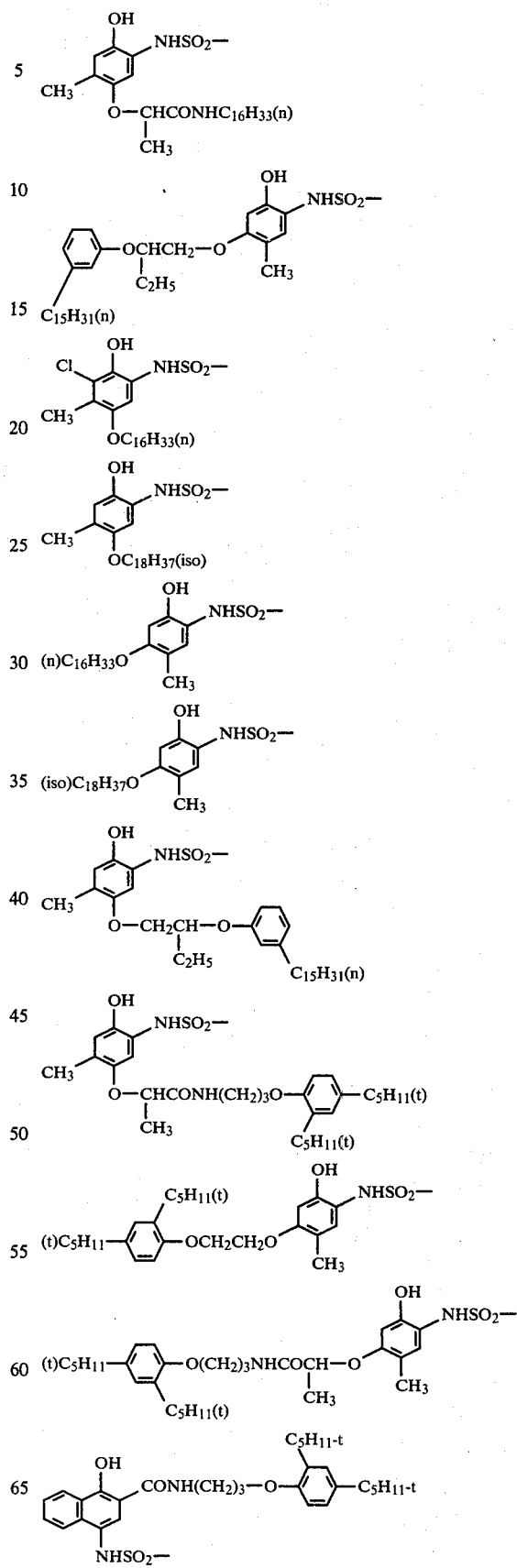

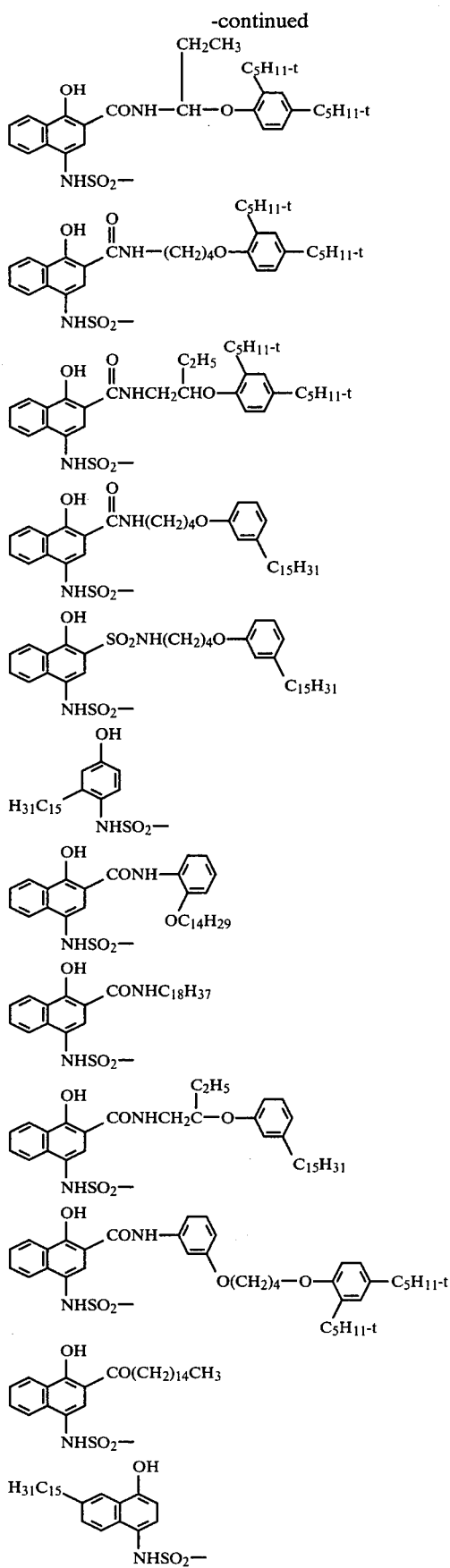

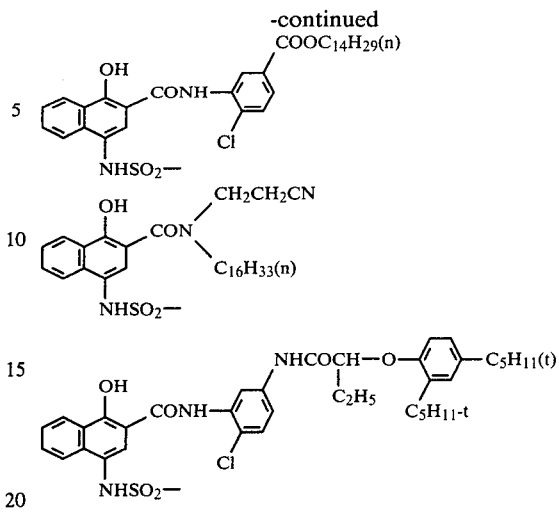

Furthermore, the groups described in Research Disclosure, Vol. 130, No. 13024 (Feb., 1975) are useful for Y.

A preferred compound according to the present invention is a compound represented by the above-described general formula (I) or (II), and in which $R^1$ represents a —$CH_2CH_2$— group; $R^{2a}$ and $R^{2b}$, which may be the same or different, each represents a straight chain or branched chain alkyl group having 1 to 4 carbon atoms (for example, a methyl group, an ethyl group, an n-propyl group, an isopropyl group, an n-butyl group, etc.).

$Q^1$ represents a hydrogen atom or a sulfamoyl group represented by the formula —$SO_2NR^3R^4$, wherein $R^3$ and $R^4$, which may be the same or different, each represents a hydrogen atom, an alkyl group including unsubstituted alkyl groups having 1 to 4 carbon atoms and substituted alkyl groups having 1 to 4 carbon atoms in the alkyl moiety, with examples of suitable substituents in the substituted alkyl group including a cyano group, an alkoxy group, a hydroxy group, a carboxy group, a sulfo group, etc., and also $R^3$ and $R^4$ can combine directly or through an oxygen atom to form a 5- or 6-membered ring.

$Q^2$ represents a hydroxy group or an —$NHSO_2R^{4a}$ group substituted at the 5-position, wherein $R^{4a}$ has the same meaning as $R^4$ defined immediately above except $R^{4a}$ cannot be a hydrogen atom; and Y represents a sulfamoyl group represented by the general formula (III).

A particularly preferred compound according to the present invention is a compound represented by the above-described general formula (I), and in which $R^{1a}$ represents a —$CH_2CH_2$— group; $R^{2a}$ represents a straight chain or branched chain alkyl roup having 1 to 4 carbon atoms.

$Q^1$ represents a hydrogen atom or a sulfamoyl group represented by the formula —$SO_2NR^3R^4$, wherein $R^3$ and $R^4$, which may be the same or different, each represents a hydrogen atom, an unsubstituted alkyl group having 1 to 4 carbon atoms or a substituted alkyl group having 1 to 4 carbon atoms in the alkyl moiety, with examples of suitable subsituents for the substituted alkyl group for $R^3$ and $R^4$ including a cyano group, an alkoxy group, a hydroxy group, a carboxy group, a sulfo group, etc., and also $R^3$ and $R^4$ can combine directly or through an oxygen atom to form a 5- or 6-membered ring.

$Q^2$ represents a hydroxy group or an $-NHSO_2R^{4a}$ group, wherein $R^{4a}$ has the same meaning as $R^4$ defined immediately above except $R^{4a}$ cannot be a hydrogen atom, at the 5-position.

Y represents an o-hydroxyphenylsulfamoyl group having an alkyl group at the meta position to the hydroxy group in addition to a ballast group.

Specific examples of dye image-providing material according to the present invention are illustrated below. However, the present invention should not be construed as being limited to these specific examples.

Compound 1

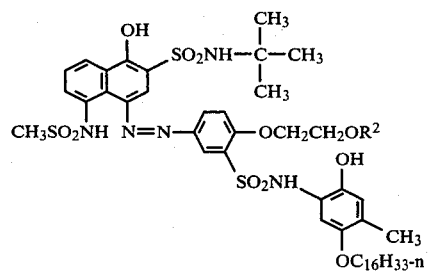

wherein $R^2$ is $CH_3$

Compound 2

Same compound as Compound 1 except for $R^2$ is $C_2H_5$.

Compound 3

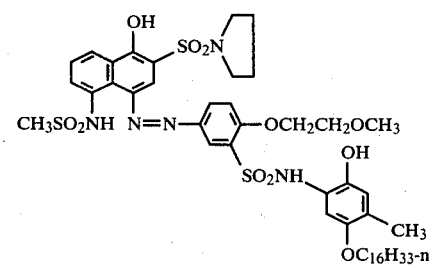

Compound 4

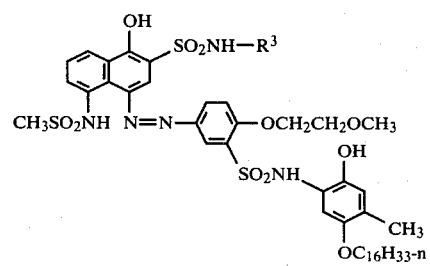

wherein $R^3$ is H

Compound 5

Same compound as Compound 4 except for $R^3$ is $CH_3$.

Compound 6

Same compound as Compound 4 except for $R^3$ is $n-C_4H_9$.

Compound 7

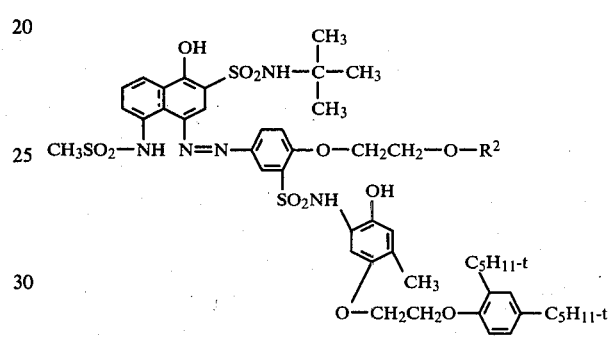

wherein $R^2$ is $CH_3$

Compound 8

Same compound as Compound 7 except for $R^2$ is $C_2H_5$.

Compound 9

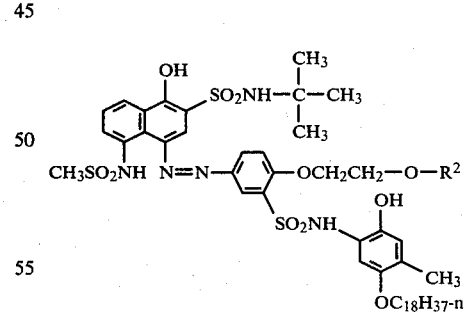

wherein $R^2$ is $CH_3$

Compound 10

Same compound as Compound 9 except for $R^2$ is $C_2H_5$.

Compound 11

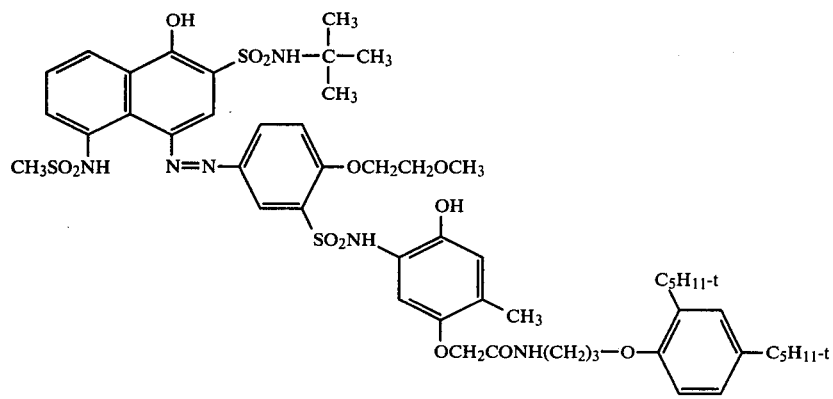
Compound 12
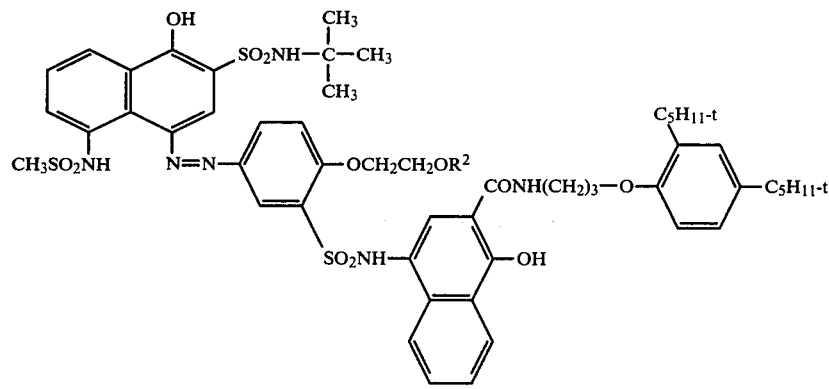
wherein R² is CH₃
Compound 14
Compound 13
Same compound as Compound 12 except for R² is C₂H₅.
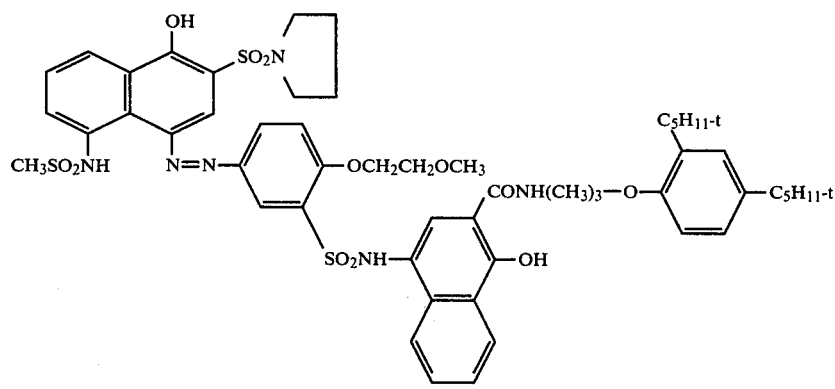

Compound 15

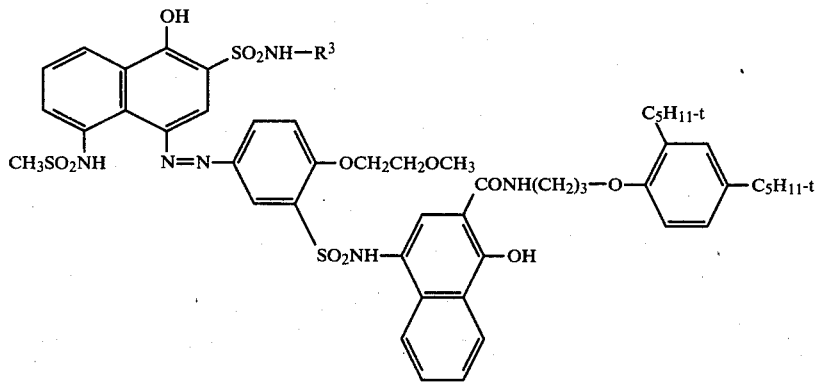

wherein R³ is H

Compound 16

Same compound as Compound 15 except for R³ is CH₃.

Compound 17

Same compound as Compound 15 except for R³ is n—C₄H₉.

Compound 18

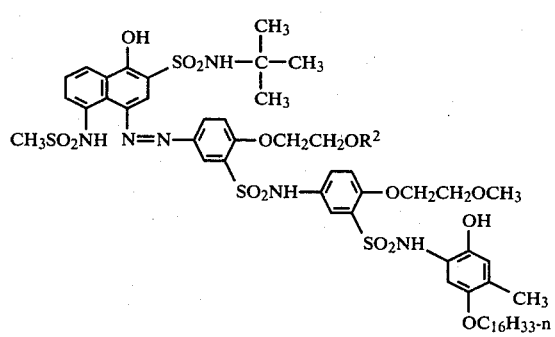

wherein R² is CH₃

Compound 19

Same compound as Compound 18 except for R² is C₂H₅.

Compound 20

Compound 21

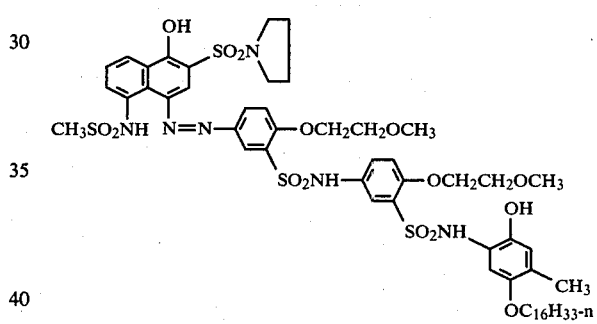

Compound 22

Same compound as Compound 21 except for R³ is CH₃.

Compound 23

Same compound as Compound 21 except for R³ is n-C₄H₅.

Compound 24

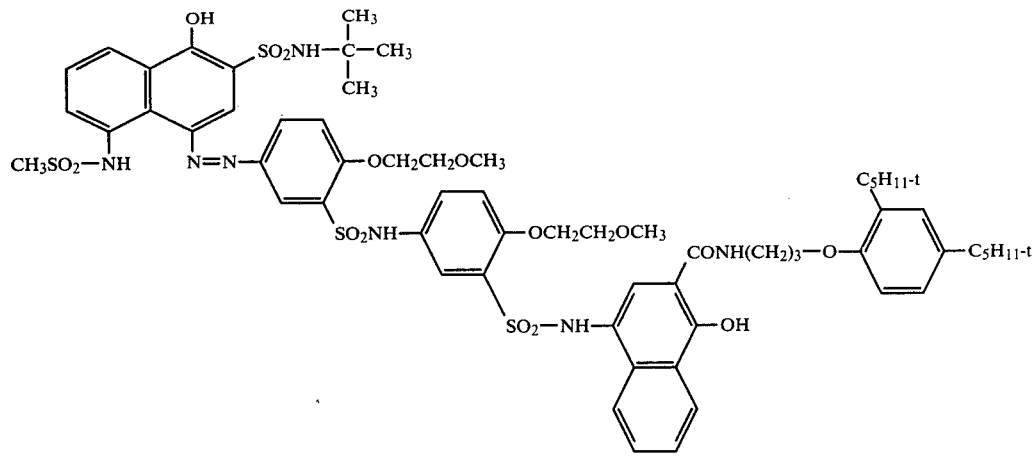

Compound 25

Same compound as Compound 4 except for $R^3$ is $C_2H_5-$.

Compound 26

Same compound as Compound 4 except for $R^3$ is $CH_3OCH_2CH_2-$.

Compound 27

Same compound as Compound 4 except for $R^3$ is $-CH(CH_3)_2$.

Compound 28

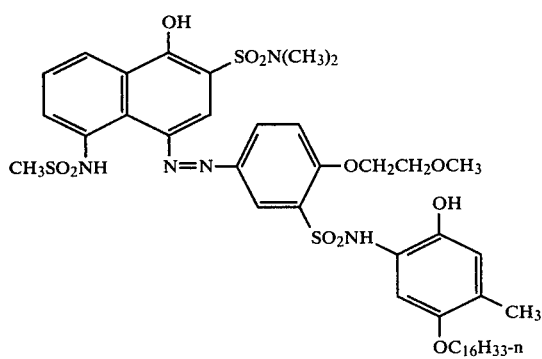

Compound 29

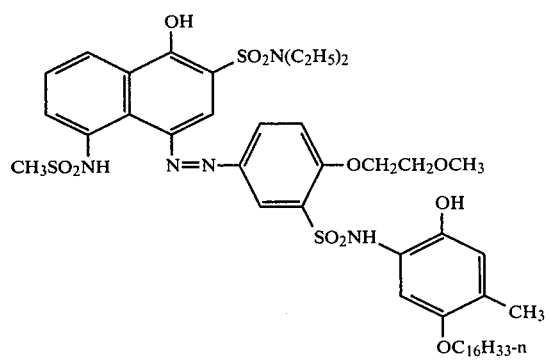

Compound 30

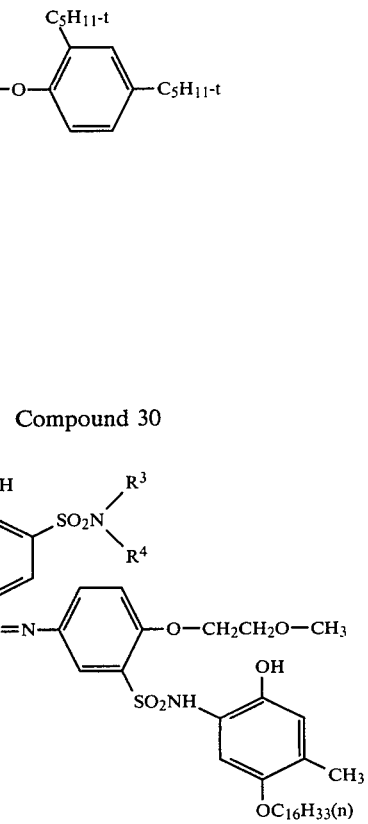

wherein $R^3$ is H and $R^4$ is cyclopentyl

Compound 31

Same compound as Compound 30 except for $R^3$ is H and $R^4$ is cyclohexyl.

Compound 32

Same compound as Compound 30 except for $R^3$ is H and $R^4$ is

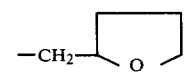

Compound 33

Same compound as Compound 30 except for $R^3$ is H and $R^4$ is

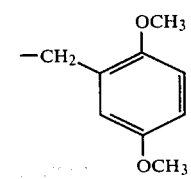

Compound 34

Same compound as Compound 30 except for $R^3$ is H and $R^4$ is —CH$_2$-CH=CH$_2$.

Compound 35

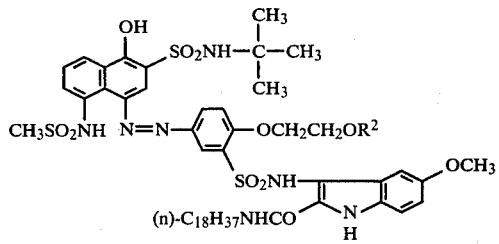

wherein $R^2$ is CH$_3$

Compound 36

Same compound as Compound 35 except for $R^2$ is C$_2$H$_5$.

Compound 37

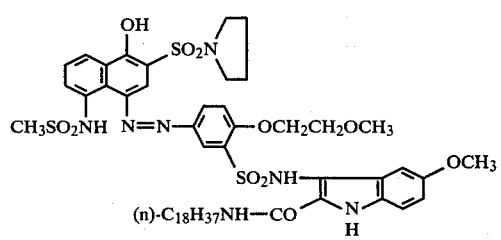

Compound 38

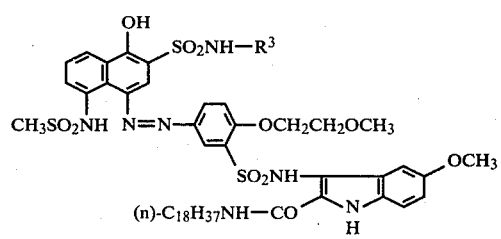

wherein $R^3$ is H

Compound 39

Same compound as Compound 38 except for $R^3$ is CH$_3$.

Compound 40

Same compound as Compound 38 except for $R^3$ is (n)—C$_4$H$_9$.

Compound 41

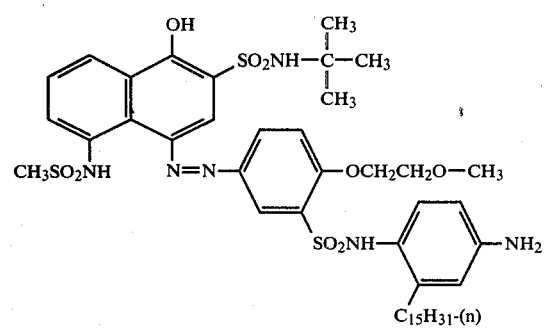

Compound 42

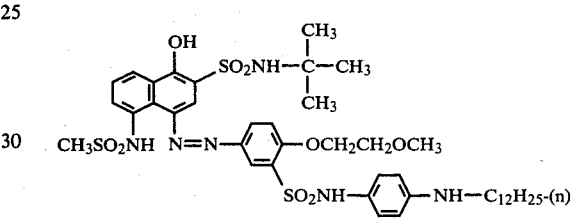

Compound 43

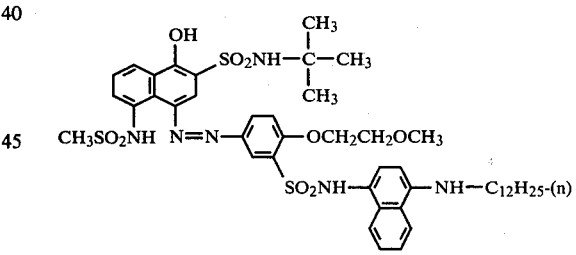

Compound 44

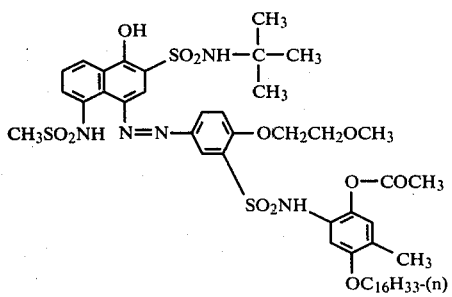

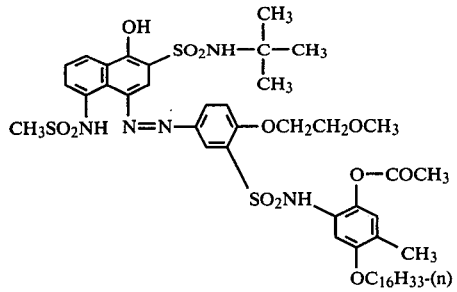
Compound 45
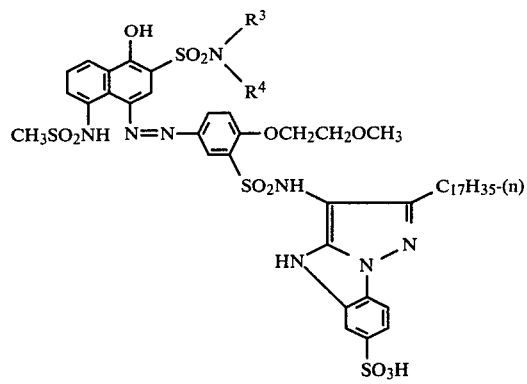
Compound 47
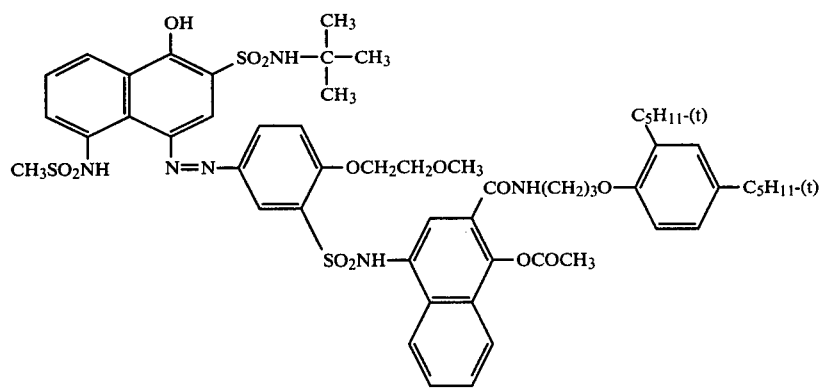
Compound 46
wherein $R^3$ and $R^4$ are $CH_3$
Compound 48
Same compound as Compound 47 except for $R^3$ and $R^4$ are $C_2H_5$.
Compound 49
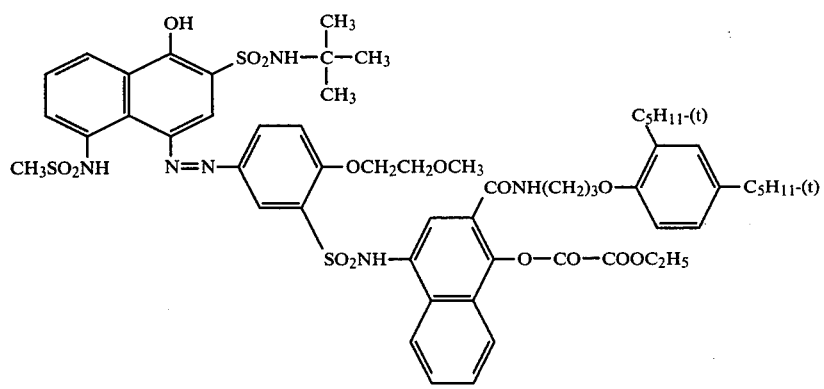

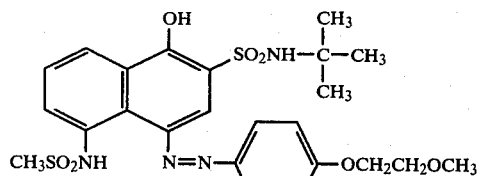
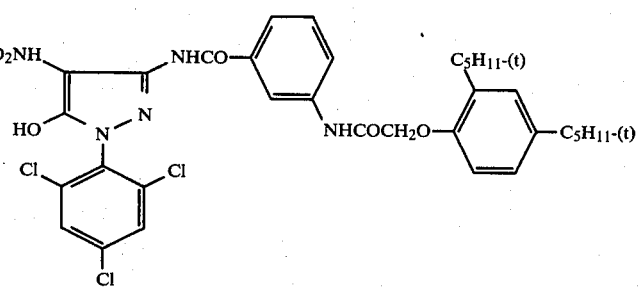

Compound 50

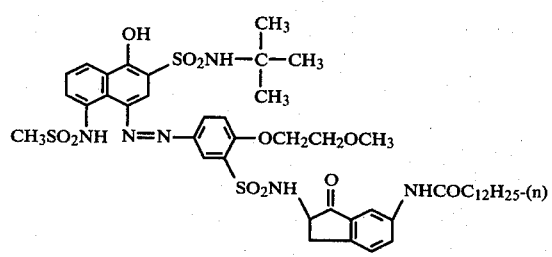

Compound 51

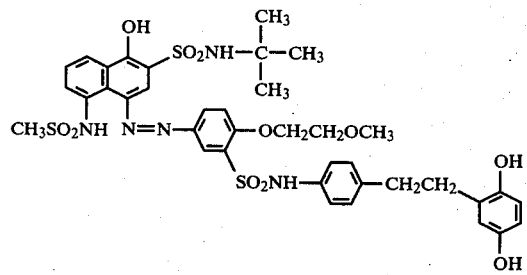

Compound 52

The preferred dye-releasing redox compound according to the present invention releases a novel magenta dye compound represented by the following formula (VIII) or (IX):

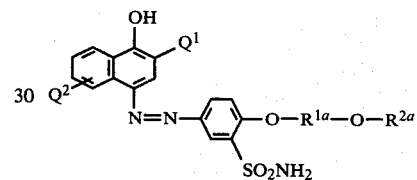
(VIII)

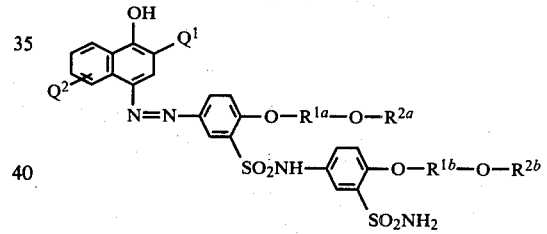
(IX)

wherein $Q^1$, $Q^2$, $R^1$ and $R^2$ each has the same meaning as defined in the general formula (I) or (II), when the compound is oxidized under alkaline conditions.

The preferred compound according to the present invention can be obtained by a condensation reaction of a sulfonyl halide represented by the formula (X) with an amine represented by the formula (XI) or (XII):

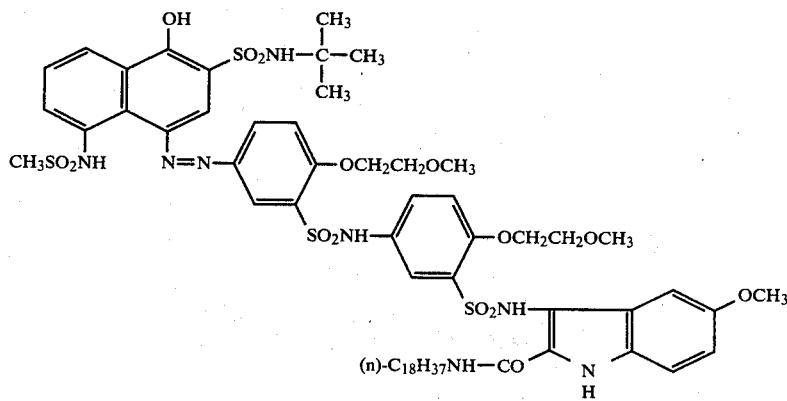

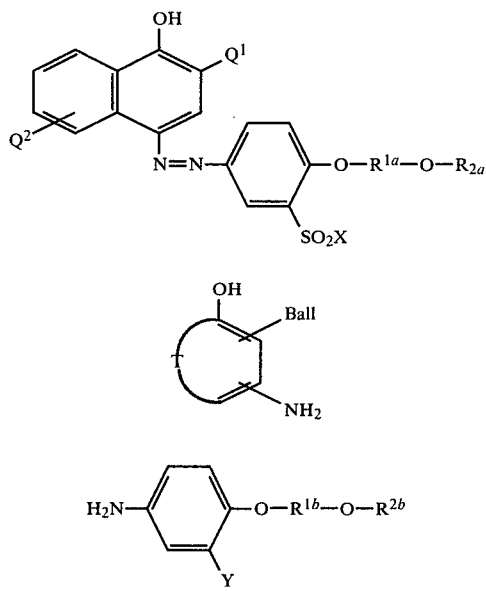

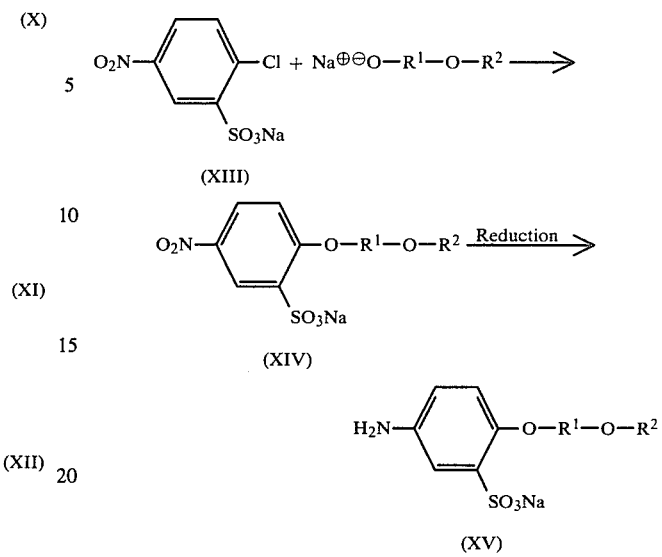

wherein $Q^1$, $Q^2$, $R^1$, $R^2$ and Y each has the same meaning as defined in the formula (I) or (II); T and Ball each has the same meaning as defined in the formula (III); and X represents a halogen atom (for example, a chlorine atom, a fluorine atom, etc.). The other compounds of the present invention can be easily prepared by methods analogous to that set forth below.

In general, the condensation reaction is preferably carried out in the presence of a basic compound at about −20° to about 200° C., preferably about 0° to about 100° C., more preferably 0° to 50° C. Examples of suitable basic compounds which can be employed include a hydroxide of an alkali metal or an alkaline earth metal (for example, sodium hydroxide, potassium hydroxide, barium hydroxide, calcium hydroxide, etc.), an aliphatic amine (for example, triethylamine, etc.), an aromatic amine (for example, N,N-diethylamine, etc.), a heteroaromatic amine (for example, pyridine, quinoline, α-, β- or γ-picoline, lutidine, collidine, 4-(N,N-dimethylamino)pyridine, etc.), or a heterocyclic base (for example, 1,5-diazabicyclo[4,3,0]nonene-5, 1,8-diazabicyclo[5,4,0]undecene-7, etc.). A heteroaromatic amine is particularly preferred of the above-described basic compounds where a compound represented by the formula (X) wherein X is a chlorine atom, that is, a sulfonyl chloride is used. Suitable solvents for the reaction are: ketonic solvents (e.g., acetone, methyl ethyl ketone, etc.), ethereal solvents (e.g., diethyl ether, tetrahydrofuran, dioxane, 1,2-diethoxyethane, diethyleneglycol dimethyl ether, 1,3-dioxolane, etc.), amides solvents (e.g., N,N-dimethylformamide, N,N-dimethylacetamide, N-methylpyrrolidone, etc.), haloalkanes (e.g., chloroform, dichloromethane, 1,2-dichloroethane, etc.) and so on.

A diazo component represented by the formula (XV) below which is required for the preparation of the compound represented by the formula (X) can be synthesized in the following manner:

wherein $R^1$ and $R^2$ each has the same meaning as defined in the formula (I) or (II).

The first step is a reaction of a compound of the formula (XIII) (sold by Hoechst Aktiengesellschaft) with an $R^2$—O—$R^1$—O− moiety. The latter is obtained by treating an alcohol of the formula $R^2$—O—$R^1$—OH with metallic sodium or sodium hydride. The reaction for obtaining a compound of the formula (XIV) is preferably carried out using an excess amount of the alcohol of the formula $R^2$—O—$R^1$—OH as a solvent. The alkoxide of the formula $R^2$—O—$R^1$—ONa is used in an amount of from about 1 mol to about 50 mol, preferably from about 1 mol to about 10 mol, and more preferably, from about 1 mol to about 3 mol, per mol of the compound having the formula (XIII). A suitable reaction temperature ranges from about −20° C. to about 150° C., preferably from 0° C. to 100° C., and more preferably from 30° C. to 85° C., in order to control the formation of by-products. The compound represented by the general formula (XIII) and the alcohol used in this synthesis are also commerically available compounds.

Another method for obtaining a compound of the formula (XIV) is to suspend a compound of the formula (XIII) in an alcohol of the formula $R^2$—O—$R^1$—OH which is used as a solvent, and to react with sodium hydroxide in the presence of manganese dioxide or sodium silicate ($Na_2O \cdot nSiO_2$ wherein n is about 1 to about 3). More particularly, 1 mol of a compound of the formula (XIII) and from about 10 g to about 1 kg, preferably from about 10 g to about 500 g, more preferably from about 30 g to about 100 g, of manganese dioxide are suspended in from about 100 ml to about 50 l, preferably from about 300 ml to about 5 l, more preferably from about 400 ml to about 2 l, of an alcohol having the formula $R^2$—O—$R^1$—OH and then treated with from about 1 mol to about 50 mol, preferably from about 1 mol to about 10 mol, more preferably from about 1 mol to about 3 mol, of sodium hydroxide. In this method, a preferred reaction temperature ranges from about 0° C. to about 150° C., more preferably from 0° C. to 100° C., most preferably from 30° C. to 85° C. This method is preferred over the former since an inflammable material such as metallic sodium or sodium hydride is not used.

Preferable compounds represented by general formula (XV) are those wherein $R^1$ represents —CH$_2$CH$_2$— and $R^2$ represents a straight or branched chain alkyl group having 1 to 4 carbon atoms. More preferable compounds are those wherein $R^1$ in the general formula represents —CH$_2$—CH$_2$— and $R^2$ represents a straight alkyl group having 1 to 4 carbon atoms. Still more preferable compounds are those wherein $R^1$ in the general formula represents —CH$_2$—CH$_2$— and $R^2$ represents a methyl group or an ethyl group.

Specific examples of the compounds represented by general formula (XV) are illustrated below.

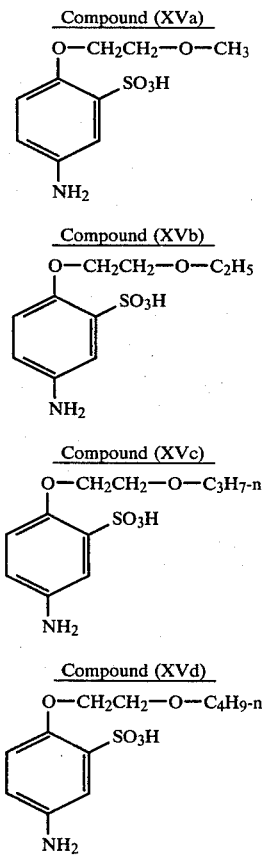

As the methods for reducing the nitro group of the compounds represented by general formula (XIV) to obtain compounds (I), reduction with iron dust, catalytic hydrogenation (Raney nickel or palladium-carbon catalyst), and hydrazine reduction (Raney nickel, palladium-carbon or active carbon catalyst) are typical. Other methods for reducing the nitro group to the amino group are described in, for example, R. B. Wagner et H. D. Zook, *Synthetic Organic Chemistry*, Chap. 24, pp. 654–657 (John Wiley, New York (1953)), S. R. Sanlder et W. Karo, *Organic Functional Group Preparations*, Chap. 13, pp. 339–345 (Academic Press, London, (1968)), and the like. These methods are also effective for synthesizing compounds of general formula (XV).

The method for reducing the nitro group of the compound represented by formula (XIV) to obtain compound (XV) will be described in more detail taking the method of reducing with iron dust for instance. About 1 mol to about 100 mols, preferably about 1 mol to about 50 mols, more preferably about 1 mol to about 10 mols, of iron dust (commercially available reduced iron or the like being preferable) is used per 1 mol of the compound represented by general formula (XIV). As the solvent for the reduction reaction, water and alcohols (e.g., methanol, ethanol, methoxyethanol, etc.) are preferable. It is also possible to use there solvents in combination. Further, ammonium chloride is desirably added as a reaction initiator in a slight amount (about 1/100 to about 1/10, preferably about 1/100 to about 1/20, of the weight of the compound of general formula (XIV)). The temperature of the above-described reaction is desirably maintained at about 30° C. to about 150° C., preferably about 50° C. to about 100° C. The thus obtained reaction solution is filtered to remove insolubles and, upon pouring the filtrate into a poor solvent (e.g., isopropyl alcohol), sodium salt of the compound of general formula (XV) is precipitated. Also, when the filtered reaction solution described above is neutralized with conc. hydrochloric acid, there can be obtained the compound of general formula (XV) as an inner salt.

An azo dye represented by the formula (XVIII) below can be obtained by diazotizing a diazo component represented by the formula (XV) and coupling it with a compound represented by the formula (XVI), i.e., a coupler or a coupling component. (The coupler component is described in, for example, U.S. Pat. No. 3,954,476.)

Diazotization of compound (XV) can be conducted according to the methods described in, for example, Yutaka Hosoya, *Shin Senryo Kagaku* (*Ney Dye Chemistry*), (Gihodo, (1963)), pp. 114–120, or Hiroshi Horiguchi, *Sosetsu Gosei Senryo* (*Review on Synthetic Dyes*), (Sankyo Shuppan (1970)), pp. 114–124. Above all, it is preferable to diazotize diazo component (XV) according to a method usually called the reversal method. In this method, 1 mol of diazo component (XV), about 1 mol of sodium nitrate and about 1 mol of sodium hydroxide (or hydroxide of other alkali or alkaline earth metal) are dissolved in water, and this mixture is added to a cooled mineral acid aqueous solution (e.g., dilute hydrochloric acid, dilute sulfuric acid, etc.). As the amounts of sodium nitrite and sodium hydroxide, the above-described amounts are preferable, though they may be added in excess amounts. The thus obtained solution of diazonium salt is mixed with an aqueous solvent solution or aqueous solution containing about 1 mol of the coupler of general formula (XVI) to conduct the coupling reaction. As the organic solvents for dissolving the coupler, water-miscible solvents are preferable. For example, alcohols (e.g., methanol, ethanol, 2-propanol, methoxyethanol, ethoxyethanol, etc.), carbonamides (e.g., N,N-dimethylacetamide, N,N-dimethylformamide, etc.), carboxylic acids (e.g., acetic acid, propionic acid, etc.) are preferable. It is also possible to dissolve the coupler of general formula (XVI) in the mixture of these solvents. Further, the coupler of general formula (XVI) may be used as an alkaline aqueous solution. Upon this coupling reaction, it is preferable to allow a basic material to coexist. As the preferable basic material, there are illustrated sodium acetate, potassium acetate, sodium hydroxide, potassium hydroxide, sodium carbonate, potassium carbonate, sodium hydrogencarbonate, etc. Details of the coupling reaction will be described hereinafter. Descriptions of the foregoing Horiguchi's book, pp. 124–129, H. E. Fierz-David et L. Blangy, *Fundamental Process of Dye Chemistry*, (Interscience Publishers Inc., New York (1949)), pp. 239–297, and K. Venkataraman, *The Chemistry of Synthetic Dyes*

(Academic Press Inc., New York (1952)), Chap. 11 are also instructive.

A compound represented by the formula (X) is prepared by converting the sulfonic acid group of the azo dye to a sulfonyl halide using a halogenating agent.

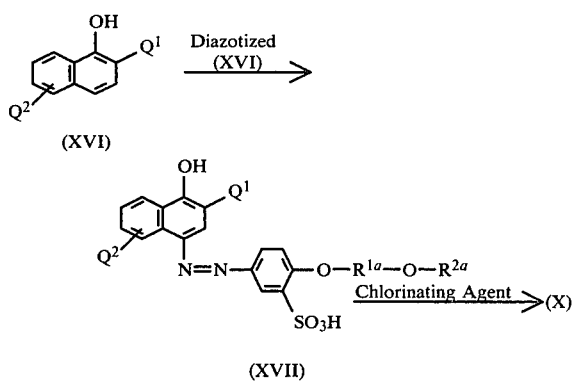

wherein $Q^1$, $Q^2$, $R^{1a}$ and $R^{2a}$ each has the same meaning as defined in the formula (I) or (II).

In order to convert the compound of the formula (XVII) to a compound of the formula (X), a chlorinating agent such as phosphorus oxychloride (POCl₃), thionyl chloride (SOCl₂) or phosphorus pentachloride (PCl₅) is preferably used. The chlorination reaction is preferably carried out in the presence of an N,N-di-substitued carbonamide such as N,N-dimethylacetamide, N,N-dimethylformanide, N-methylpyrrolidone, etc., as a catalyst.

In particular, compounds wherein X represents chlorine are preferable. Synthesis of such compounds will now be described. As the chlorinating agent for converting a sulfonic acid group in general formula (XVII) to chlorosulfonyl group, there are illustrated the agents above-described. This reaction proceeds smoothly in the presence of a carboxlic acid amide such as N,N-dimethylacetamide, N,N-dimethylformamide, N-methylpyrrolidone, etc. The necessary amount of the above-described chlorinating agent is a stoichiometric amount but, in many cases, it is desirable to use it in excess (1.5 to 50 times, preferably 1.5 to 10 times the theoretical amount). In most cases, this reaction proceeds at room temperature (about 25° C.). Where the reaction is too vigorous, it is possible to cool it to about 0° C. On the other hand, where the reaction proceeds too slowly, the reaction system may be heated within the range of 25° to 1502 C. (preferably 25° to 100° C.).

Compounds wherein X represents other halogen can also be synthesized according to the method described in *Houben-Weyls Methoden der Organishen Chemie*, edited by E. Müller, Vol. IX, pp. 557-598 (1958).

Typical examples of the amine represented by the formula (XI) are described, for example, in U.S. Pat. Nos. 4,055,428, 3,932,380 and 3,931,144 and *Research Disclosure*, Vol. 130, No. 13024.

A typical method for the preparation of the amine represented by the formula (XII) is schematically illustrated below:

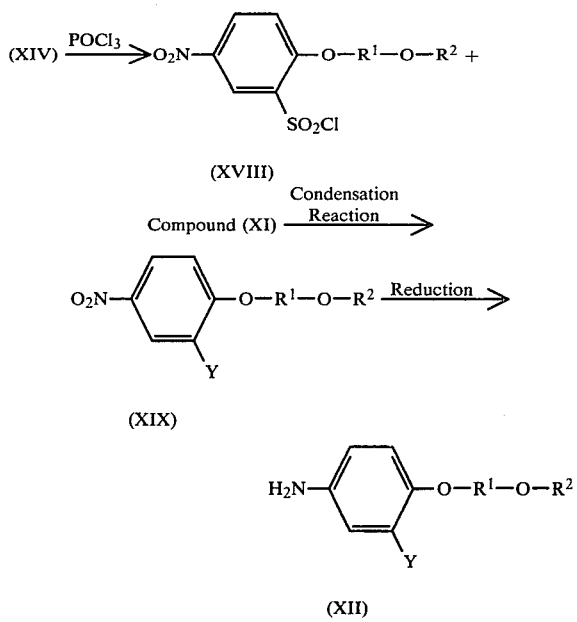

wherein $R^1$, $R^2$ and Y each has the same meaning as defined in the formula (II).

In order to obtain a compound represented by the formula (XVIII) from a compound represented by the formula (XIV), chlorinating agent such as those described in the preparation of the compound of the formula (X) described above can be used. In this case, the reaction is preferably carried out in the presence of an N,N-di-substituted carbon amide.

The condensation reaction of the sulfonyl chloride represented by the formula (XVIII) and an o- or p-hydroxyarylamine having a ballast group bonded thereto represented by the formula (XI) to obtain a compound of the formula (XIX) is preferably carried out in the presence of a basic compound, with suitable examples of basic compounds being as described with respect to the reaction of the compound of the formula (X) with the compound of the formula (XI) or (XII).

Typical examples of reduction reactions for obtaining a compound represented by the formula (XII) include a catalystic hydrogenation (e.g., using Raney nickel, palladium-carbon or charcoal as a catalyst), a reduction with iron powder, a reduction with hydrazine, etc. It should be emphasized that, in the compound of the formula (XII), the basicity of the amino group is increased due to the presence of the $R^{2b}$—O—$R^{1b}$—O— group. Accordingly, the following condensation reaction of the compound of the formula (XII) with a sulfonyl halide of the formula (X) proceeds easily.

Typical synthesis examples of the dye-releasing redox compounds used in the present invention and intermediates.

SYNTHESIS EXAMPLE 1

Synthesis of Sodium 2-(2-Methoxyethoxy)-5-nitrobenzenesulfonate

[Method 1]

To a solution of sodium 2-methoxyethylate prepared by adding 7.3 g of sodium hydride (14.6 g of a 50% suspension in liquid paraffin) to 330 ml of methyl Cellosolve, was added 55 g of sodium 2-chloro-5-nitrobenzenesulfonate with stirring. The reaction mixture was heated at 80° to 85° C. on a water bath with stirring for 30 minutes. After filtering the mixture while hot, 1.5 liters of isopropyl alcohol was added to the filtrate. The crystals thus-precipitated were recovered by filtration and washed with 100 ml of isopropyl alcohol. Yield: 59 g; Melting Point: 238° to 239° C.

[Method 2]

A mixture of 5.2 g of sodium 2-chloro-5-nitrobenzenesulfonate, 0.6 g of manganese dioxide, 15 ml of methyl Cellosolve, 1 ml of water and 0.95 g of sodium hydroxide was stirred at 75° C. for 40 minutes. After cooling, the insoluble materials were removed by filtration and the filtrate was poured into 100 ml of isopropyl alcohol. The crystals thus-precipitated were recovered by filtration to obtain 4.8 g of sodium 2-(2-methoxyethoxy)-5-nitrobenzenesulfonate. Melting Point: 238° to 239° C.

[Method 3]

Using the same procedure as described in Method 2 above except that 0.8 g of sodium silicate (No. 3, $Na_2O \cdot n\ SiO_2$ wherein n is about 3) was used in place of the manganese dioxide, 4.8 g of sodium 2-(2-methoxyethoxy)-5-nitrobenzenesulfonate was obtained. Similar results were obtained using $Na_2O \cdot n\ SiO_2$ wherein n is about 1, about 2 and about 2.5, respectively.

SYNTHESIS EXAMPLE 2

Synthesis of Sodium 2-(2-Ethoxyethoxy)-5-nitrobenzenesulfonate

To a solution of sodium 2-ethoxyethylate prepared by adding 7.3 g of sodium hydride (14.6 g of 50% suspension in liquid paraffin) to 300 ml of ethyl Cellosolve was added 55 g of sodium 2-chloro-5-nitrobenzenesulfonate. The reaction mixture was heated at 80° to 85° C. with stirring for 30 minutes. After completion of the reaction, the insoluble materials were removed by filtration and from the filtrate 150 ml of ethyl Cellosolve was distilled off under reduced pressure. To the concentrated solution was added 300 ml of isopropyl alcohol and the mixture was cooled with ice. The crystals which thus precipitated were recovered by filtration, washed with 100 ml of isopropyl alcohol and air-dried. Yield: 33 g; Melting Point: 248° to 249° C.

SYNTHESIS EXAMPLE 3

Synthesis of Sodium 2-(2-Butoxyethoxy)-5-nitrobenzenesulfonate

The above compound was obtained in the same manner as described in Method 2 of Synthesis Example 1 except that ethylene glycol monobutyl ether was used in place of the methyl Cellosolve. Melting Point: 104° to 106° C.

SYNTHESIS EXAMPLE 4-1

Synthesis of Sodium 5-Amino-2-(2-methoxyethoxy benzenesulfonate

A mixture solution of 30 g of sodium 2-(2-methoxyethoxy)-5-nitrobenzenesulfonate, 30 g of reduced iron, 0.6 g of ammonium chloride and 60 ml of water was heated at 80 to 85° C. with stirring for 2 hours. After completion of the reaction, the insoluble materials were removed by filtration, 200 ml of isopropyl alcohol was added to the filtrate and the mixture was cooled with ice. The crystals thus precipitated were collected by filtration, washed with 50 ml of isopropyl alcohol and air-dried. Yield: 23 g; Melting Point: above 250° C.

SYNTHESIS EXAMPLE 4-2

Synthesis of Compound (XVa)

A mixture solution of 20 g of sodium 2-(2-methoxyethoxy)-5-nitrobenzenesulfonate obtained in Synthesis Example 1, 10 g of reduced iron, 0.4 g of ammonium chloride, 40 ml of isopropyl alcohol and 40 ml of water was stirred for 90 minutes at 77° C. After completion of the reaction, insolubles were removed by filtration, and 20 ml of conc. hydrochloric acid (36%) was added to the filtrate. Crystals thus formed were collected by filtration, washed with 50 ml of isopropyl alcohol, and air-dried. Yield: 19.6 g; Melting Point: 286°-289° C.

| Elemental Analysis | H | C | N |
|---|---|---|---|
| Calcd. for $C_9H_{15}NO_6S$ (%): (monohydrate) | 5.70 | 40.74 | 5.28 |
| Found (%): | 5.50 | 41.02 | 5.18 |

SYNTHESIS EXAMPLE 4-3

Synthesis of Compound (XVb)

A mixed solution of 10 g of sodium 2-(2-ethoxyethoxy)-5-nitrobenzenesulfonate obtained in Synthesis Example 2, 5 g of reduced iron, 0.2 g of ammonium chloride, 20 ml of isopropyl alcohol and 20 ml of water was stirred for 2 hours at 77° C. After completion of the reaction, insolubles were removed by filtration, and 10 ml of conc. hydrochloric acid (36%) was added to the filtrate. Crystals thus formed were collected by filtration, washed with 30 ml of isopropyl alcohol, and air-dried. Yield: 7.6 g; Melting Point: 278°-283° C.

| Elemental Analysis | H | C | N |
|---|---|---|---|
| Calcd. for $C_{10}H_{15}NO_5S$ (%): | 5.79 | 45.97 | 5.36 |
| Found (%): | 5.73 | 45.86 | 5.24 |

SYNTHESIS EXAMPLE 4—4

Synthesis of Compound (XVc)

A mixture solution of 10 g of sodium 2-(2-propoxyethoxy)-5-nitrobenzenesulfonate, 5 g of reduced iron, 0.2 g of ammonium chloride, 20 ml of isopropyl alcohol and 20 ml of water was stirred at 77° C. for 2 hours. After completion of the reaction, insolubles were removed by filtration, and 10 ml of conc. hydrochloric acid (36%) was added to the filtrate. Crystals thus formed were collected by filtration, and air-dried. Yield: 7.1 g; Melting Point: 287°-290° C.

| Elemental Analysis | H | C | N |
|---|---|---|---|
| Calcd. for $C_{11}H_{17}NO_5S$ (%): | 6.22 | 47.99 | 5.09 |
| Found (%): | 6.11 | 47.41 | 4.99 |

SYNTHESIS EXAMPLE 5

(1) Synthesis of 2-(N-tert-Butylsulfamoyl)-4-[4-(2-methoxyethoxy)-5-sulfophenylazo]-5-methanesulfonamido-1-naphthol To a solution containing 1.7 g of sodium hydroxide and 8 ml of water, 9.9 g of sodium 5amino-2-methoxyethoxy)benzenesulfonate and then 10 ml of an aqueous solution containing 2.8 g of sodium nitrite were added. The solution was added dropwise to a solution containing 18 ml of conc. hydrochloric acid and 70 ml of water at a temperature below 5° C. The mixture was stirred for 30 minutes at below 5° C. to complete the reaction.

To a solution containing 8.0 g of sodium hydroxide, 40 ml of water and 150 ml of methyl alcohol, 14.9 g of 2-tert-butylsulfamoly-5-methanesulfonamido-1-naphthol was added. To the solution thus prepared, the above described diazo solution was added dropwise at a temperature below 10° C. After completion of the addition, the mixture was stirred for 30 minutes at below 10° C. and 20 ml of concentrated hydrochloric acid was added thereto. The crystals thus precipitated were collected by filtration, washed with 200 ml of acetone and air-dried. Yield: 19 g; Melting Point: 215°–220° C.

In manner analogous to Step (1) in synthesis Example 5, the compounds tabulated below were also synthesized.

(XVIIa)

| Compound No. | $R^3$ | $R^4$ | m.p. (°C.) |
|---|---|---|---|
| XVII-1 | —CH$_3$ | H | >250 |
| XVII-2 | —C$_2$H$_5$ | H | >250 |
| XVII-3 | —CH(CH$_3$)$_2$ | H | >250 |
| XVII-4 | —C$_2$H$_5$ | C$_2$H$_5$ | 195–203 |
| XVII-5 | —C$_3$H$_7$(n) | —C$_3$H$_7$(n) | 163–168 |
| XVII-6 | —(CH$_2$)$_4$—* | | >250 |
| XVII-7 | —C$_6$H$_5$ | H | >250 |
| XVII-8 | —CH$_3$ | —CH$_3$ | >250 |
| XVII-9 | —C$_4$H$_9$(n) | —C$_4$H$_9$(n) | 156–160 |
| XVII-10 | —CH$_2$CH$_2$OCH$_3$ | H | 248–250 |

*$R^3$ and $R^4$ are combined to form —(CH$_2$)$_4$—

(2) Synthesis of 2-(N-tert-Butylsulfamoly)-4-[4-(2-methoxyethoxy)-5-chlorosulfonylphenylazo]-5-methanesulfonamido-1-naphthol To a solution containing 19 g of 2-(N-tert-butylsulfamoyl)-4-[4-(2-methoxyethoxy)-5-sulfophenylazo]-5-methanesulfonamido-1-naphthol prepared as described in Step (1) above, 100 ml of acetone and 20 ml of phosphorous oxychloride, 20 ml of N,N-dimethylacetamide was added dropwise at a temperature below 50° C. After completion of the addition, the mixture was stirred for 1 hour and was poured gradually into 500 ml of ice water. The crystals thus precipitated were collected by filtration, washed with 50 ml of acetonitrile and air-dried. Yield: 14 g; Melting Point: 148°–153° C.

In the manner analogous to Step (2) in Synthesis Example 5, the compounds tabulated below were also synthesized.

(Xa)

| Compound No. | $R^3$ | $R^4$ | m.p. (°C.) |
|---|---|---|---|
| X-1 | —CH$_3$ | H | 115–120 |
| X-2 | —C$_2$H$_5$ | H | 190–194 |
| X-3 | —CH(CH$_3$)$_2$ | H | 175–177 |
| X-4 | —C$_2$H$_5$ | —C$_2$H$_5$ | 167–168 |
| X-5 | —C$_3$H$_7$(n) | —C$_3$H$_7$(n) | 153–155 |
| X-6 | —(CH$_2$)$_4$—* | | 184–187 |
| X-7 | —C$_6$H$_5$ | H | 115–120 |
| X-8 | —CH$_3$ | —CH$_3$ | 200–205 |
| X-9 | —C$_4$H$_9$(n) | —C$_4$H$_9$(n) | 156–160 |

*$R^3$ and $R^4$ are combined to form —(CH$_2$)$_4$—.

(3) Synthesis of Compound 1

To 40 ml of N,N-dimethylacetamide, 20 g of 2-amino-4-hexadecyloxy-5-methylphenol hydrochloride and 13 g of 2-(N-tert-butylsulfamoyl)-4-[4-(2-methoxyethoxy)-5-chlorosulfoxylphenylazo]-5-methanesulfonamido-1-naphthol prepared as described in Step (2) above were added. 10 ml of pyridine was added dropwise to the mixture with stirring and the mixture was stirred at room temperature for 2 hours. The reaction mixture was poured into a mixture of 10 ml of hydrochloric acid and 200 ml of ice water. The crystals thus precipitated were collected by filtration, washed with water, air-dried and recrystallized from 50 ml of methyl alcohol. Yield: 5.0 g; Melting Point: 140°–142° C.

SYNTHESIS EXAMPLE 6

(1) Synthesis of 2-Pyrrolidinosulfonyl-4-[4-(2-methoxyethoxy)-5-sylfophenylazo]-5-methanesulfonamido-1-naphthol To a solution containing 0.9 g of sodium hydroxide and 40 ml of water, 4.9 g of sodium 5-amino-2-(2-methoxyethoxy)benzenesulfonate and then 5 ml of aqueous solution containing 1.4 g of sodium nitrite were added. The solution was added dropwise to a solution containing 9 ml of concentrated hydrochloric acid and 36 ml of ice water at a temperature below 5° C. The mixture was stirred for 30 minutes at below 5° C. to complete the reaction.

To a solution containing 4.0 g of sodium hydroxide, 20 ml of water and 40 ml of methyl alcohol, 7.4 g of 2-pyrrolidinylsulfamoyl-5-methanesulfonamido-1-naphthol was added. To the solution thus prepared, the above-described diazo solution was added dropwise at a temperature below 10° C. After completion of the addition, the mixture was stirred for 30 minutes and 10 ml of concentrated hydrochloric acid was added thereto. The crystals thus precipitated were collected by filtration, washed with 100 ml of acetone and air-dried. Yield: 8.7 g; Melting Point: above 250° C.

(2) Synthesis of 2-Pyrrolidinosulfonyl-4-[4-(2-methoxyethoxy)-5-chlorosulfonylphenylazo]-5-methanesulfonamido-1-naphthol To a solution containing 8.7 g of 2-pyrrolidionosulfonyl -4-[4-(2-methoxyethoxy)-5-sulfophenylazo]-5-methanesulfonamido-1-naphthol prepared as described in Step (1) above, 40 ml of acetone and 9 ml of phosphorous oxychloride, 9 ml of N,N-dimethylacetamide was added dropwise at a temperature below 50° C. After completion of the addition, the mixture was stirred fo 1 hour at room temperature and was poured into 200 ml of ice water. The crystals thus precipitated were collected by filtration and washed with 20 ml of acetonitrile. Yield: 5.0 g; Melting Point: 184°–187° C.

(3) Synthesis of Compound 3

To 20 ml of N,N-dimethylacetamide, 3.1 g of 2-amino-4-hexadecyloxy-5-methylphenol hydrochloride and 5.0 g of 2-pyrrolidinosulfonyl-4-[4(2-methoxyethoxy)-5-chlorosulfonylphenylazo]-5-methanesulfonamido-1-naphthol prepared as described in Step (2) above were added. 3.6 ml of pyridine was added dropwise to the mixture with stirring and the mixture was stirred at room temperature for 2 hours. After completion of the reaction, 30 ml of methanol and 10 ml of water were added to the reaction solution. The crystals thus precipitated were collected by filtration, washed with 50 ml of methanol, air-dried and recrystallized from 50 ml of acetonitrile. Yield: 4.0 g; Melting Point: 105°–108° C.

SYNTHESIS EXAMPLE 7

Synthesis of Compound 18

(a) Synthesis of 2-(2-Methoxyethoxy)-5-nitrobenzenesulfonly Chloride 59 g of sodium 2-(2-methoxyethoxy)-5-nitrobenzenesulfonate prepared as described in Synthesis Example 1 was added to a mixture of 200 ml of acetone and 75 ml of phosphorous oxychloride. 75 ml of N,N-dimethylacetamide was added dropwise to the mixture with stirring while the reaction mixture was maintained at 30° to 40° C. After completion of the addition, the mixture was allowed to stand with stirring until it cooled to room temperature. The reaction mixture was then poured into 600 ml of ice water, stirred for 30 minutes and the crystals thus precipitated were collected by filtration. The crystals were washed with 100 ml of water and air-dried. Yield: 56 g; Melting Point: 74°–74.5° C.

(b) Synthesis of 2-[2'-(2-Methoxyethoxy)-5'-nitrobenzenesulfonamido]-4-hexadecyloxy-5-methylphenol 20 g of 2-amino-4-hexadecyloxy-5-methylphenol hydrochlorid and 18 g of 4-(2-methoxyethoxy)nitrobenzene-3-sulfonyl chlroide prepared as described in Step (a) above were added to a mixture of 100 ml of tetrahydrofuran and 10 ml of pyridine and the mixture was stirred at room temperature for 3 hours. The reaction mixture was added to a mixture of 300 ml of ice water and 50 ml of concentrated hydrochloric acid with stirring. The crystals thus-precipitated were recovered with filtration, washed with water, air-dried and recrystallized from 100 ml of acetonitrile. Yield: 35 g; Melting Point: 85.5°–86° C.

(c) Synthesis of 2-[2'-(2-Methoxyethoxy)-5'-aminobenzenesulfonamido]-4-hexadecyloxy-5-methylphenol 32 g of 2-[2'(2-methoxyethoxy)-5'-nitrobenzenesulfonamido]-4-hexadecyloxy-5-methylphenol prepared as described in Step (b) above, 24 g of iron powder, 12 g of $Fe_2O_4$, 0.6 g of ammonium chloride and 25 ml of water were added to 300 ml of isopropyl alcohol and the mixture was refluxed on a stream bath with stirring for 1 hour. After completion of the reaction, the mixture was filtered while hot and the filtrate was cooled with ice. The crystals thus precipitated were recovered by filtration, washed with 50 ml of isopropyl alcohol and air-dried. Yield: 23 g; Melting Point: 142° to 144° C.

(d) Synthesis of Compound 18

To 10 ml of N,N-dimethylacetamide, 3.8 g of 2-tert-butylsulfamoyl-4-[4-(2-methoxyethoxy)-5-chlorosulfonylphenylazo]-5-methanesulfonamido-1-naphthol prepared as described in Step (2) of Synthesis Example 5 and 3.5 g of 2-[2-(2-methoxyethoxy)-5-aminobenzenesulfonamido]-4-hexadecyloxy-5-methylphenol prepared as described in Step (c) above was added. 1.8 ml of pyridine was added dropwise to the mixture and the mixture was stirred at room temperature for 2 hours. After completion of the reaction, 15 ml of methanol and 5 ml of water were added to the reaction solution. The crystals thus precipitated were collected by filtration and recrystallized from 50 ml of methanol. Yield: 4.0 g; Melting Point: 117°–123° C.

SYNTHESIS EXAMPLE 8

Synthesis of Compound 20

To 15 ml of N,N-dimethylacetamide, 6.5 g of 2-pyrrolidinosulfonyl-4-[4-(2-methoxyethoxy)-5-chlorosulfonylphenylazo]-5-methanesulfonamido-1-naphthol prepared as described in Step (2) of Synthesis Example 6 and 5.9 g of 2-[2-(2-methoxyethoxy)-5-aminobenzenesulfonamido]-4-hexadecyloxy-5-methylphenol prepared as described in Step (c) of Synthesis Example 7 were added. 1.6 ml of pyridine was added dropwise to the mixture and the mixture was stirred at room temperature for 2 hours. After completion of the reaction, 20 ml of methanol and 10 ml of water were added to the reaction mixture. The crystals thus precipitated were collected by filtration, washed with 50 ml of methanol, air-dried and recrystallized from 200 ml of acetonitrile. Yield: 9.5 g; Melting Point; 143°–146° C.

In the reproduction of natural color by subtractive color photography, a light-sensitive element comprising at least two combinations of each of a silver halide emulsion having a selective spectral sensitivity in a certain wavelength region and a compound capable of providing a dye having a selective spectral absorption at the same wavelength region as the emulsion is used. In particular, a light-sensitive element comprising a combination of a blue-sensitive silver halide emulsion and a compound capable of providing a yellow dye, a combination of a green-sensitive silver halide emulsion and a compound capable of providing a magenta dye, and a combination of a red-sensitive silver halide emulsion and a compound capable of providing a cyan dye is useful. As a matter of course, diffusible dye-releasing redox compounds of the present invention can be used as the abovedescribed compounds capable of providing the dye. These combinations of units of the silver halide emulsions and the dye providing compounds may be coated on a support as layers in a face-to-face relationship or may be coated on a support as a layer containing a mixture of particles of the silver halides and the dye providing compounds in a binder.

In a preferred multilayer structure, a blue-sensitive silver halide emulsion layer, a green-sensitive silver halide emulsion layer and a red-sensitive silver halide emulsion layer are positioned in this order from the side of incident light of exposure and, in particular, it is desirable for a yellow filter layer to be positioned between the blue-sensitive silver halide emulsion layer and the green-sensitive silver halide emulsion layer when a highly sensitive silver halide emulsion containing silver iodide is used. The yellow filter layer usually contains a dispersion of yellow colloidal silver, a dispersion of an oil-soluble yellow dye, an acid dye mordanted to a basic polymer, or a basic dye mordanted to an acid polymer.

it is advantageous for the silver halide emulsion layers to be separated from each other by an interlayer. The interlayer acts to prevent the occurrence of undesirable interactions between the differently color-sensitized silver halide emulsion layers. The interlayer employed in such a case is usually composed of a hydrophilic polymer such as gelatin, polyacrylamide, a partially hydrolyzed product of polyvinyl acetate, etc., a polymer containing fine pores formed from a latex of a hydrophilic polymer and a hydrophobic polymer, e.g., as described in U.S. Pat. No. 3,625,685, or a polymer whose hydrophilic property is gradually increased by the processing composition, such a calcium alginate, as described in U.S. Pat. No. 3,384,483, individually or as a combination thereof.

Generally speaking, except where noted otherwise, the silver halide emulsion layers employed in this invention comprise photosensitive silver halide dispersed in gelatin and are about 0.5 to about 20μ thick, preferably 0.6 to 6μ thick; the dye image providing materials are dispersed in an aqueous alkaline solution-permeable polymeric binder, such as gelatin, as a separate layer about 0.5 to about 20μ thick, preferably 1 to 7μ thick; and the alkaline solution-permeable polymeric interlayers, e.g., gelatin, are about 0.5 to about 20μ thick, preferably 1 to 5μ in thick. Of course, these thicknesses are approximate only and can be modified according to the product desired.

the silver halide emulsions which can be used in the present invention are a dispersion of silver chloride, silver bromide, silver chlorobromide, silver iodobromide, silver chloroiodobromide or a mixture thereof in a hydrophilic colloid. The halide composition of the silver halide is selected depending on the purpose of using the photographic materials and the processing conditions for the photographic materials, but a silver iodobromide emulsion or a silver chloroiodobromide emulsion having a halide composition of 1 to 10% iodide, less than 30 mol % chloride, and the rest bromide is particularly preferred. The grain size of the silver halide used may be a conventional grain size or a fine grain size but silver halides having a mean grain size of from about 0.1 micron to about 2 microns are preferred. Furthermore, depending on the specific purpose of using the photographic materials, it is sometimes desirable to use a silver halide having a uniform grain size. The silver halide grains used in the present invention may have the form of a cubic system, an octahedral system, or mixed crystal system thereof. These silver halide emulsions may be prepared using conventional methods as described in, for example, P. Grafkides, *Chimie Photographique,* Chapters 18–23, 2nd Edition, Paul Montel, Paris (1957).

The silver halide emulsions used in the present invention are preferably chemically sensitized, e.g., by heating using the natural sensitizers contained in gelatin, a sulfur sensitizer such as sodium thiosulfate or N,N,N'-trimethylthiourea, a gold sensitizer such as a thiocyanate complex salt or thiosulfate complex salt of gold, or a reducing sensitizer such as stannous chloride or hexamethylenetetramine.

Also, silver halide emulsions which form a latent image on the surface of the silver halide grains, silver halide emulsions which form a latent image inside the silver halide grains as described in U.S. Pat. Nos. 2,592,550, 3,206,313, etc., and direct positive silver halide emulsions can be used in the present invention.

A suitable coating amount of the emulsions ranges from about 0.1 g/m$^2$ to 10 g/m$^2$, preferably 0.3 g/m$^2$ to 4 g/m$^2$ (silver per m$^2$ of the support). A suitable amount of the dye image-providing material of this invention can range from about 0.01 to about 10 mols, preferably 0.05 to 0.5 mol, per mol of the silver halide.

The silver halide emulsions used in the present invention may be stabilized with additives such as 4-hydroxy-6-methyl-1,3,3a,7-tetrazaindene, 5-nitroimidazole, 1-phenyl-5-mercaptotetrazole, 8-chloromercuriquinoline, benzenesulfinic acid, pyrocatechin, 4-methyl-3-sulfoethylthiazolidin-2-thione, 4-phenyl-3-sulfoethylthiazolidin-2-thione, etc., if desired. In addition, inorganic compounds such as cadmium salts, mercury salts, complex salts of platinum group metals such as the chloro complex salt of palladium, and the like are also useful for stabilizing the light-sensitive material of the present invention. Furthermore, the silver halide emulsions used in the present invention may contain sensitizing compounds such as a polyethylene oxide compound.

The silver halide emulsions used in the present invention can possess, if desired, a color sensitivity expanded with a spectral sensitizing dye or dyes. Examples of useful spectral sensitizers are cyanine, merocyanine, holopolar cyanine, styryl, hemicyanine, oxanole, hemioxanole, etc., dyes. Specific examples of suitable spectral sensitizers which can be used in this invention are described in, for example, P. Grafkides, supra, Chapters 35–41, and F. M. Hamer, *The Cyanine Dyes and Related Compound,* Interscience. A particularly useful spectral sensitizer is a cyanine of which the nitrogen atom of the basic heterocyclic nucleus has been substituted with an aliphatic group (e.g., an alkyl group) having a hydroxy group, a carboxy group, or a sulfo group as described in, for example, U.S. Pat. Nos. 2,503,776, 3,459,553 and 3,177,210.

The dye image providing material used in this invention can be dispersed in a hydrophilic colloid using various techniques, depending on the type of dye image providing material. For example, when the dye image providing material has a dissociable group such as a sulfo group or a carboxy group, the dye image providing material can be added to an aqueous solution of a hydrophilic colloid as a solution in water or as an aqueous alkaline solution thereof. On the other hand, when the dye image providing material is sparingly soluble in aqueous medium but is readily soluble in organic solvents, the dye image providing material is first dissolved in an organic solvent and then the solution is finely dispersed in an aqueous solution of a hydrophilic colloid with stirring. Such a dispersing method is described in detail in, for example, U.S. Pat. Nos. 2,322,027, 2,801,171, 2,949,360 and 3,396,027.

The concentration of the dye image providing materials that are employed in the present invention may be varied over a wide range depending upon the particular compound employed and the results which are desired. For example, the dye image providing compounds of the present invention may be coated in layers by using coating solutions containing about 0.5 to about 15% by weight, preferably containing 0.5 to 8% by weight, of the dye image providing compound distributed in a hydrophilic film forming natural material or synthetic polymer, such as gelatin, polyvinyl alcohol, etc.

To stabilize the dispersion of the dye image providing material and also to promote dye image formation, it is advantageous to incorporate the dye image providing material into an aqueous hydrophilic colloid solution as a solution in a solvent which is substantially insoluble in water and has a boiling point of higher than about 200° C. at normal pressure. Examples of suitable high boiling solvents which can be used for this purpose are aliphatic esters such as the triglycerides of higher fatty acids, dioctyl adipate, etc.; phthalic acid esters such as di-n-butyl phthalate, etc.; phosphoric acid esters such as tri-o-cresyl phosphate, tri-n-hexyl phosphate, etc.; amides such as N,N-diethyllaurylamide, etc.; and hydroxy compounds such as 2,4-di-n-amylphenol. Furthermore, to stabilize the dye image providing material and to promote dye image formation, it is also advantageous to incorporate an oleophilic polymer into the photosensitive layer together with the dye image providing material. Examples of suitable oleophilic polymers which can be used for this purpose are shellac, a phenol-formaldehyde condensate, poly-n-butyl acrylate, a copolymer of n-butyl acrylate and acrylic acid, an interpolymer of n-butyl acrylate, styrene, and methacrylamide, etc.

Such as oleophilic polymer may be dissolved in an organic solvent together with the dye image providing material and then may be dispersed in a photographic hydrophilic colloid such as gelatin as a solution thereof or may be added to a dispersion in a hydrophilic colloid of the dye-releasing redox compound as the hydrosol of a polymer prepared by emulsion polymerization, etc.

The ratio of dye image-providing material to polymer can be about 0.1 to about 10, preferably about 0.25 to about 5.

The dispersion of the dye image providing material is generally carried out using a large shearing stress. For instance, a high speed mixer, a colloid mill, a high pressure milk homogenizer, a high pressure homogenizer as described in British Pat. No. 1,304,264, an ultrasonic emulsifying device, etc., are suitably used.

The dispersion of the dye image providing material can be greatly promoted by using a surface active agent as an emulsification aid. Examples of suitable surface active agents useful for dispersion of the dye image providing material used in this invention are sodium triisopropylnaphthalenesulfonate, sodium dinonylnaphthalenesulfonate, sodium p-dodecylbenzenesulfonate, sodium dioctylsulfosuccinate, sodium cetylsulfate, and the anionic surface active agents as described in Japanese Patent Publication No. 4,293/1964 and British Patent 1,138,514. The use of these anionic surface active agents and the higher fatty acid ester of anhydrohexitol exhibits particularly excellent emulsifying capability as disclosed in U.S. Pat. No. 3,676,141. A suitable amount of the surface active agent ranges from about 1% to about 20% by weight per gram of the dye image providing material. Furthermore, the dispersing methods disclosed in Japanese Patent Publication No. 13837/1968 and U.S. Pat. Nos. 2,992,104, 3,044,873, 3,061,428 and 3,832,173 can be effectively employed for dispersing the dye image providing material used in this invention.

The light-sensitive element of the present invention is prepared by coating directly or indirectly at least one light-sensitive silver halide photographic emulsion layer with the dye image providing material according to the present invention associated therewith onto a substantially planar material which does not undergo large dimensional changes. Examples of suitable supports which can be used are cellulose acetate films, polystyrene films, polyethylene terephthalate films, polycarbonate films, etc., as are used as supports for conventional photographic materials. Other examples of suitable supports are papers and papers coated with a water-impermeable polymer such as polyethylene.

The methods described in U.S. Pat. Nos. 3,928,312, 3,931,144 and 3,954,476, and Belgian Patent 788,268 can be employed as methods of forming diffusion transfer color photographic images by using dye image providing material. These image forming methods can be effectively used with the dye image providing material according to the present invention.

One embodiment of a series of steps for obtaining color diffusion transfer images using a dye-releasing redox compound according to the present invention is described below.

(A) A light-sensitive element comprising a support having thereon at least one light-sensitive silver halide emulsion layer with the dye-releasing redox compound according to the present invention associated therewith is imagewise exposed.

(B) An alkaline processing composition is spread on the above-described light-sensitive silver halide emulsion layer whereby development of all light-sensitive silver halide emulsion layers in the presence of a developing agent for silver halide is conducted.

(C) As a result, an oxidation product of the developing agent produced in proportion to the amount of exposure cross-oxidizes the dye-releasing redox compound.

(D) The above-described oxidation product of the dye-releasing redox compound splits to release a diffusible dye.

(E) The released diffusible dye imagewise diffuses to form a transferred image on an image-receiving layer (directly or indirectly) adjacent the light-sensitive silver halide emulsion layer.

In the above-described process, any silver halide developing agents which can cross-oxidize the dye-releasing redox compound can be used. These developing agents may be incorporated into the alkaline processing composition or may be incorporated into appropriate photographic layers of the light-sensitive element. Specific examples of suitable developing agents which can be used in this invention are, for example, hydroquinones; aminophenols such as N-methylaminophenol; pyrazolidones such as 1-phenyl-3-pyrazolidone, 1-phenyl-4,4-dimethyl-3-pyrazolidone, 1-phenyl-4-methyl-4-oxymethyl-3-pyrazolidone; phenylenediamines such as N,N-diethyl-p-phenylenediamine, 3-methyl-N,N-diethyl-p-phenylenediamine, 3-methoxy-N-ethoxy-p-phenylenediamine; etc.

Of the above-indicated developing agents, black-and-white developing agents having the capability, in general, of reducing the occurrence of stains in image-receiving layers are particularly preferred in comparison with color developing agents such as phenylenediamines.

When the dye-releasing redox compound according to this invention is used, the transferred image formed in the image-receiving layer is a negative image and the image remaining in the photosensitive layer is a positive image where a conventional surface latent image forming type emulsion is used without using a reversal mechanism. On the other hand, where a direct positive silver halide emulsion (including an emulsion which can provide a direct reversal positive image by fogging during development after exposure, for example, an internal latent image forming type silver halide emulsion or a solarization type silver halide emulsion) is employed as the silver halide emulsion in the above-described case, the transferred image formed in the image-receiving layer is a positive image.

Solarization type silver halide emulsions as described in C. E. K. Mees, *The Theory of the Photographic Process*, pages 261–297, Macmillan Co., New York (1942) can be used in this invention. These solarization type silver halide emulsions may be prepared using methods described in, for example, British Pat. Nos. 443,245 and 462,730 and U.S. Pat. Nos. 2,005,837, 2,541,472, 3,367,778, 3,501,305, 3,501,306 and 3,501,307.

Also, internal latent image forming type silver halide emulsions as described in, for example, U.S. Pat. No. 2,592,250, can be advantageously used in this invention. Typical examples of fogging agents which can be used for preparing this type of silver halide emulsion are the hydrazines described in U.S. Pat. Nos. 2,588,982 and 2,563,785, the hydrazide and hydrozone described in U.S. Pat. No. 3,227,552, and the quaternary salt compounds described in British Pat. No. 1,283,835, Japanese Patent Publication No. 38164/1974, and U.S. Pat. Nos. 3,734,738, 3,719,494 and 3,615,615. The amount of fogging agent employed can be widely varied depending upon the results desired. In general, the concentration of fogging agent is from about 0.1 to about 15 g per mol of silver, preferably from about 0.4 to about 10 g per mol of silver in the photosensitive layer in the photosensitive element.

Furthermore, the diffusion inhibitor releasing (DIR) reversal silver halide emulsion system as described in U.S. Pat. Nos. 3,227,551, 3,227,554 and 3,364,022 or the reversal silver halide system using dissolution physical development as described in British Patent 904,364 can be employed in the case of using the dye-releasing redox compound of this invention.

The dye image providing material according to the present invention can be used together with a dye image providing material having an absorption in a longer wavelength region, if desired. The molar ratio of the compound of the present invention in a mixture ranges from about 1 to about 70%, preferably 1 to 50%. Compounds which provide a transferred image having an absorption maximum at 545 to 600 nm are desirable dye image providing material to be used with the compound of the present invention. A dye image providing material having an absorption in a longer wavelength region can be incorporated into a layer containing the compound according to the present invention or into another preferably adjacent layer. A dye image providing material having an absorption in a longer wavelength region is preferably changed temporarily to a compound having an absorption in a short wavelength in a dispersion in view of color reproduction.

It is necessary for the image-receiving element used in this invention in combination with the above-described light-sensitive element to have an image-receiving mordanting layer comprising a mordant, such as the poly-4-vinylpyridine latex (in, preferably, polyvinyl alcohol) described in U.S. Pat. No. 3,148,061, the polyvinyl pyrrolidone described in U.S. Pat. No. 3,003,872, and the polymers containing quaternary ammonium salts as described in U.S. Pat. No. 3,239,337, individually or as a combination thereof. Also, the basic polymers as described in U.S. Pat. Nos. 2,882,156, 3,625,694 and 3,709,690 can be effectively used as the mordant for the image-receiving layer. Other examples of mordants which can be effectively used in this invention are described in U.S. Pat. Nos. 2,484,430, 3,271,147, 3,184,309, etc.

Preferably the light-sensitive sheet of this invention is capable of neutralizing the alkali carried in from the alkaline processing composition. It is advantageous for this purpose for the light-sensitive sheet to include in a cover sheet or in an image-receiving element thereof a neutralizing layer containing an acid material in an amount sufficient to neutralize the alkali in the liquid processing composition, that is, containing an acid material at an area concentration higher than the equivalent of the alkali in the spread liquid processing composition. When a cover sheet having a neutralizing layer is used, the cover sheet can be superimposed on an image-receiving layer after such has been peeled from a light-sensitive element. Typical examples of preferred acid materials which can be used for this purpose are those described in U.S. Pat. Nos. 2,983,606, 2,584,030 and 3,362,819. The neutralizing layer may further contain a polymer such as cellulose nitrate, polyvinyl acetate, etc., and also the plasticizers as described in U.S. Pat. No. 3,557,237 in addition to the acid material. The acid material may be incorporated in the light-sensitive sheet in a microencapsulated form as described in German Patent Application (OLS) No. 2,038,254.

It is desirable for the neutralizing layer or the acid material-containing layer which can be used in this invention to be separated from the spread layer of the liquid processing composition by a neutralization rate controlling layer (or timing layer). Gelatin, polyvinyl alcohol, or the compounds described in U.S. Pat. Nos. 3,455,686, 4,009,030 and 3,785,815, Japanese Patent Application Nos. 77946/1957 and 90616/1975, Japanese Patent Application (OPI) Nos. 92022/1973, 64435/1974, 22935/1974 and 77333/1976, Japanese Patent Publication Nos. 15756/1969, 12676/1971 and 41214/1973, German patent application (OLS) Nos. 1,622,936 and 2,162,227, *Research Disclosure*, No. 151, 15162 (1967), etc., can be effectively used as the timing layer. The timing layer acts to retard the reduction in the pH of the liquid processing composition by the neutralizing layer until the desired development and transfer of dyes can be sufficiently accomplished.

In a preferred embodiment of this invention, the image-receiving element has a multilayer structure comprising a support, a neutralizing layer, a timing layer, and a mordanting layer (or image-receiving layer) in this order. Image-receiving elements are described in detail in, for example, Japanese patent application (OPI) No. 13285/1972, U.S. Pat. No. 3,295,970 and British Pat. No. 1,187,502.

The processing composition of the present element used in this invention is a liquid composition containing the processing components necessary for developing silver halide emulsions and forming diffusion transfer dye images. The solvent of the processing composition is mainly water and contains, as the case may be, a hydrophilic solvent such as methanol, methyl Cellosolve, etc. The liquid processing composition contains alkali in an amount sufficient to maintain the necessary pH on developing the silver halide emulsion layers and for neutralizing acids (e.g., hydrohalic acids such as hydrobromic acid, etc., and carboxylic acids such as acetic acid, etc.) formed during development and dye image formation. Examples of suitable alkalis are hydroxides or salts of ammonia, alkali metals or alkaline earth metals or amines, such as lithium hydroxide, sodium hydroxide, potassium hydroxide, an aqueous dispersion of calcium hydroxide, tetramethylammoniumhydroxide, sodium carbonate, trisodium phosphate, diethylamine, etc. It is desirable for the liquid processing composition to contain an alkaline material in a concentration such that the pH thereof can be maintained at above about 12, in particular, above 14 at room temperature. Further preferably, the liquid processing composition contains a hydrophilic polymer such as high molecular weight polyvinyl alcohol, hydroxyethyl cellulose, sodium carboxymethyl cellulose, etc. These polymers contribute toward increasing the viscosity of the liquid processing compositiom above about 1 poise, preferably to 500 or 600 to 1,000 poises, at room temperature, which facilitates the uniform spreading of the processing composition at development as well as the formation of a non-fluid film when the aqueous medium has diffused into the photosensitive element and the image-receiving element during processing thereby concentrating the processing composition, which results in assisting unification of all of the elements after processing. The polymer film also contributes toward preventing coloring components from transferring into the image-receiving layer to stain the dye images formed after the formation of the diffusion transfer dye image is substantially completed.

As the case may be, it is advantageous for the liquid processing composition to further contain a light absorbing material such as $TiO_2$, carbon black, a pH indicating dye, etc., or the desensitizer as described in U.S. Pat. No. 3,579,333 for preventing the silver halide emulsion layers from being fogged by ambient light during processing outside the camera. Furthermore, the liquid processing composition used in this invention may contain a development inhibitor such as benzotriazole.

It is preferred for the above-described processing composition to be retained in a rupturable container as described in U.S. Pat. Nos. 2,543,181, 2,643,886, 2,653,732, 2,723,051, 3,056,491, 3,056,492, 3,152,515, etc.

As the developer, any developer that can cause the oxidation-reduction reaction between exposed silver halide and the DRR compound may be used. For example, ordinary color developers or black-and-white developers are included. Of these, black-and-white developers are particularly preferable. In the case of using a diffusible dye-releasing compound with other dye image-providing materials, all that is required is to use a conventional color developer upon processing in a manner with which the artisan is well acquainted. Where a dye developing agent is used as the dye image-providing material, it is not necessary to use other developing agents upon processing. However, it is preferable to use an auxiliary developing agent (e.g., an ordinary black-and-white developing agents).

The light-sensitive film unit of the present invention which has a construction such that after imagewise exposure, the processing of the film unit is performed by passing the film unit through a pair of juxtaposed pressure-applying membes comprises:

(1) a support,
(2) a light-sensitive element as described above,
(3) an image-receiving element as described above,
(4) a processing element as described above, and
(5) a developing agent (which can be incorporated into the processing element or the light-sensitive element).

According to one embodiment of the film unit described above, the light-sensitive element and the image-receiving element are superimposed in a face-to-face relationship, and the unit is processed, after exposure, by spreading an alkaline processing composition between both elements. In this case, the image-receiving element may be stripped off after the transfer of the dye images has been completed or the dye images formed in the image-receiving layer may be observed without stripping the image-receiving element as described in U.S. Patent 3,415,645.

In another embodiment of the film unit as described above, the image-receiving element and the light-sensitive element are positioned in this order in the film unit on a support. For example, a suitable photographic film unit is prepared by coating on a transparent support an image-receiving layer, a substantially opaque light reflecting layer (for example, a $TiO_2$-containing layer and a carbon black-containing layer) and a single or a plurality of light-sensitive layers as described above, in this order, as disclosed in Belgian Pat. No. 757,960. After exposing the light-sensitive element, the light-sensitive element is superimposed on an opaque cover sheet in a face-to-face relationship and then a liquid alkaline processing composition is spread between them.

Another embodiment of the superimposed and integral type film unit to which the present invention is most preferably applicable is disclosed in Belgian Pat. No. 757,959. According to this embodiment, the film unit is prepared by coating on a transparent support an image-receiving layer, a substantially opaque light reflective layer (as described above), and a single or a plurality of light-sensitive layers as described above, in this order, and further superimposing a transparent cover sheet on the light-sensitive layer in a face-to-face relationship. A rupturable container retaining an alkaline processng composition having incorporated therein a light-intercepting agent such as, for example, carbon black, is disposed adjacent to and between the uppermost layer of the above-described light-sensitive element and the transparent cover sheet. The film unit is imagewise exposed in a camera through the transparent cover sheet and then the rupturable container retaining the alkaline processing composition is ruptured by the pressure-applying members when the film unit is withdrawn from the camera to spread uniformly the processing composition containing the opacifying agent between the light-sensitive layer and the cover sheet, whereby the film unit is shielded from light and development proceeds.

In these embodiments of film units, the neutralization mechanism as described above is preferably incorporated therein. In particular, the neutralizing layer is preferably positioned in the cover sheet and, further, the timing layer is positioned on the side toward where the processing solution is to be spread, if desired.

Moreover, other useful embodiments of the integral type of film units wherein the dye image providing material of this invention can be used are described in, for example, U.S. Pats. Nos. 3,415,644, 3,415,645, 3,415,646, 3,647,487, and 3,635,707 and German Patent Application (OLS) No. 2,426,980.

The present invention can provide advantageous effects and some of these, particularly, due to the introduction of $R^2-O-R^1-O-$ group, are described below.

Firstly, color images having less light-fading are obtained because of the superiority in the light fastness of the dyes released.

Secondly, color images with high quality are obtained when the dye-releasing redox compound according to the present invention is used together with other redox compounds of good hue, since the hue of the dyes released is excellent and does not vary with changes of pH.

Thirdly, the amount of dyes remaining at exposed areas in light-sensitive elements is very small, since the transferability of the dye released is excellent. Therefore, it is effective to obtain negative color images composed of the unreacted dye image providing material which are obtained by stripping off the light-sensitive element and subjecting it to bleach processing (i.e, the negative can be easily used).

Fourthly, the dyes released are hardly subjected to fadng in a dark place due to a vinyl monomer such as acrylic acid or butylacrylate which is present in a neutralizing layer.

The following examples are given to further illustrate this invention in greater detail.

EXAMPLE 1

Dye Compound A represented by the following formula:

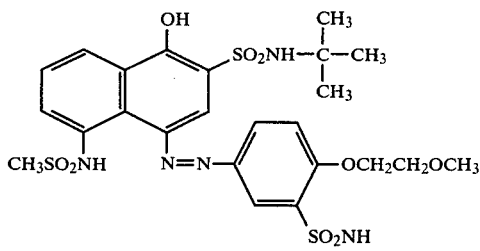

which is released from Compound 1 according to the present invention was dissolved in N,N-dimethylformamide (DMF) to prepare a $10^{-3}M$ solution. 0.25 ml of the solution was diluted with 11.5 ml of DMF and a mixture of 1.25 ml of a $10^{-1}M$ solution of butylacrylate and 12.5 ml of a buffer having a pH of 5.05 (Britton-Robinson Buffer) was added thereto. The solution was allowed to stand at room temperature (25°–29° C.) and the decrease of absorbance at a maximum absorption wavelength in a visible region was measured. Assuming that the decrease of dye A can be shown by a pseudo first order equation, a reaction rate constant of the pseudo first order reaction, i.e., k was determined.

The procedure described above and the remaining rate of dye and the reaction rate constant (k) were determined with respect to Dye Compound B represented by the following formula:

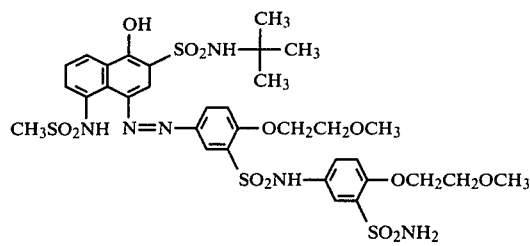

which is released from Compound 18 according to the present invention.

For comparison, the remaining rate of dye and the reaction rate constant (k) were determined in the same manner described above with respect to Comparison Compounds C to E below:

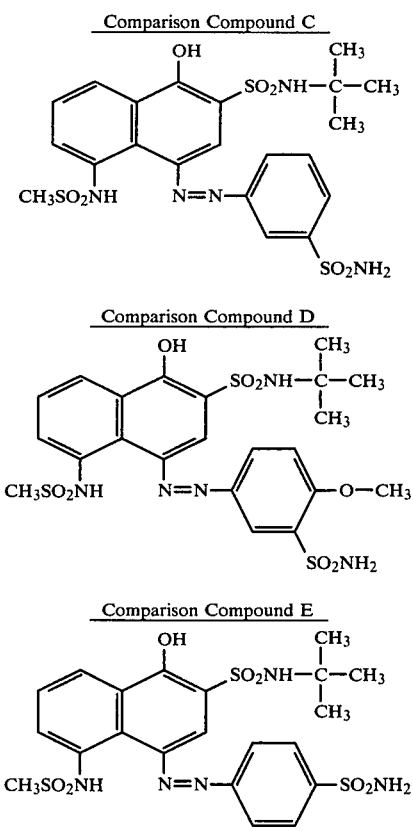

The results obtained are shown in Table 1 below.

TABLE 1

| Reaction of Released Dye Compound with Butylacrylate | |
|---|---|
| Compound | k |
| | (day$^{-1}$) |
| A | 0.027 |
| B | 0.023 |
| C (comparison) | 0.072 |
| D (comparison) | 0.048 |
| E (comparison) | 0.098 |

It is apparent from the results shown in Table 1 that Compounds A and B according to the present invention have a remarkably excellent fastness in comparison with Comparison Compounds C to E.

EXAMPLE 2

On a polyethylene terephthalate transparent support were coated the layers described below in the order listed to prepare a light-sensitive sheet.

(1) Mordanting layer containing 3.0 g/m² of a mordant shown below:

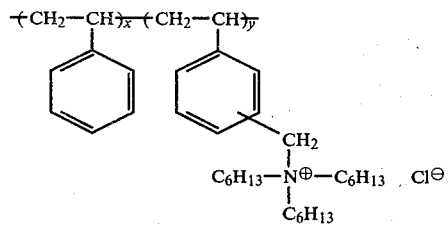

x:y=50:50 (molar ratio) and 3.0 g/m² of gelatin.

(2) White light reflective layer containing 20 g/m² of titanium oxide and 2.0 g/m² of gelatin.

(3) Light-shielding layer containing 2.70 g/m² of carbon black and 2.70 g/m² of gelatin.

(4) Layer containing 0.80 g/m² of the magenta dye releasing redox compound shown in Table 2, 0.40 g/m² of N,N-diethyl-laurylamide and 1.08 g/m² of gelatin.

(5) Layer containing a green-sensitive internal latent image type direct positive silver iodobromide emulsion (halogen composition in the silver halide: 1 mol% of iodide; silver amount: 1.8 g/m²; gelatin: 1.3 g/m²), 0.028 g/m² of a fogging agent represented by the following formula:

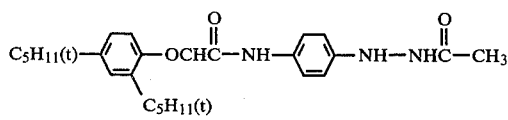

and 0.13 g/m² of sodium dodecylhydroquinone sulfonate.

(6) Layer containing 0.94 g/m² of gelatin.

Also, processing solution and a cover sheet shown below were prepared.

| Processing Solution: | |
|---|---|
| 1-Phenyl-4-methyl-4-hydroxymethyl-3-pyrazolidinone | 10 g |
| Methylhydroquinone | 0.18 g |
| 5-Methylbenzotriazole | 4.0 g |
| Sodium Sulfite (anhydrous) | 1.0 g |
| Carboxymethyl Cellulose Na Salt | 40.0 g |
| Carbon Black | 150 g |
| Potassium Hydroxide (28% aq. soln.) | 200 cc |
| $H_2O$ | 550 cc |

The processing solution of the above composition was filled into a container rupturable with pressure by 0.8 g each.

Cover Sheet:

On a polyethylene terephthalate support were coated an acid polymer layer (neutralizing layer) containing 15 g/m² of polyacrylic acid (a 10 wt% aq. soln. having viscosity of about 1,000 cp) and a timing layer containing 3.8 g/m² of acetyl cellulose (hydrolysis of 100 g of acetyl cellulose forms 39.4 g of acetyl groups), and 0.2 g/m² of a styrene-maleic anhydride copolymer (composition (molar) ratio: styrene: maleic anhydride=about 60:40; molecular weight: about 50,000) to prepare a cover sheet.

Processing Step:

The above described cover sheet was superimposed on the above described light-sensitive sheet to form a film unit. Exposure was performed through a wedge having stepwise different density from the cover sheet side. Then, the processing solution described above was spread between both sheets in a thickness of 85 microns (the spreading was performed with assistance of a pressure roller). The processing was carried out at 25° C. After processing, the transferred images were observed through the transparent support of the light-sensitive sheet. The maximum density and the minimum density of the magenta transferred images formed were measured one hour after the processing. Further, the remaining ratio of magenta color image after allowing to stand the film unit thus processed for 2 weeks at 60° C. and 100% relative humidity (fading in a dark place) and the remaining ratio of magenta color image after exposed the film until thus processed to a light of 17,000 lux for 3 days using a fluorescent lamp fading tester (light-fading) were determined. The results thus obtained are shown in Table 2.

TABLE 2

| Magenta Dye Releasing Redox Compound | $D_{max}$ | $D_{min}$ | Fading in a Dark (remaining ratio) | Light Fading (remaining ratio) | Remarks |
|---|---|---|---|---|---|
| Compound 1 | 1.71 | 0.24 | 0.79 | 0.90 | This invention |
| Compound 3 | 1.80 | 0.23 | 0.70 | 0.84 | This invention |
| Compound 20 | 1.73 | 0.23 | 0.73 | 0.85 | This invention |
| Compound X[1] | 1.63 | 0.24 | 0.65 | 0.89 | Comparison |
| Compound Y[2] | 1.62 | 0.24 | 0.43 | 0.75 | Comparison |

[1]Compound in which the $CH_3OCH_2CH_2O$- group in Compound 1 is substituted with a hydrogen atom.
[2]Compound in which the $CH_3OCH_2CH_2O$- group in Compound 3 is substituted with a hydrogen atom.

It is apparent from the results shown in Table 2 that magenta color images having a high maximum density and an excellent stability are obtained when the compounds according to the present invention are used. Further, the magenta dye imges transferred from the compounds according to the present invention have an excellent hue and varies only to a small extent with changes of pH (from 4 to 9).

EXAMPLE 3

On a polyethylene terephthalate transparent support, the layers described below in the order listed to prepare a light-sensitive sheet.

(1) Mordant-containing layer described in Example 2.
(2) Titanium oxide-containing layer described in Example 2.
(3) Carbon black-containing layer described in Example 2.
(4) Layer containing a cyan dye releasing redox compound shown below (0.50 g/m²), N,N-diethyl-laurylamide (0.25 g/m²) and gelatin (1.14 g/m²).

[Structure: 4-hydroxy-8-amino-naphthalene with azo linkage to phenyl bearing NO₂ and SO₂CH₃ groups]

[Yellow dye releasing redox compound structure with SO₂NH-phenyl-OCH₂CH₁OCH₃, SO₂NH, OH, CH₃, OC₁₆H₃₃, pyrazolone ring with NC, N, phenyl, C=O, C=N-NH linking to OCH₃-phenyl-SO₂NH-phenyl-OCH₂CH₂OCH₃-SO₂NH-phenyl with OH, CH₃, OC₁₆H₃₃]

(5) Layer containing a red-sensitive internal latent image type direct positive silver iodobromide emulsion (halogen composition in the silver halide: 2 mol% of iodide; silver amount: 1.9 g/m²; gelatin: 1.4 g/m²), a fogging agent same as described in Example 2 (0.028 g/m²) and sodium dodecylhydroquinone sulfonate (0.13 g/m²).

(6) Layer containing gelatin (2.6 g/m²) and 2,5-di-tertpentadecylhydroquinone (0.8 g/m²).

(7) Layer containing compound 3 of the present invention (0.45 g/m²), diethylenelaurylamide (0.10 g/m²), 2,5-di-tertbutylhydroquinone (0.0074 g/m²) and gelatin (0.76 g/m²).

(8) Layer containing a green-sensitive internal latent image type direct positive silver iodobromide emulsion (halogen composition in the silver halide: 2 mol % of iodide; silver amount: 1.4 g/m²; gelatin: 1.0 g/m²), a fogging agent same as described in Example 2 (0.024 g/m²) and sodium dodecylhydroquinone sulfonate (0.11 g/m²).

(9) Layer containing gelatin (2.6 g/m²) and sodium dodecylhydroquinone (0.8 g/m²).

(10) Layer containing a yellow dye releasing redox compound shown below (0.80 g/m²), diethyllaurylamide (0.16 g/m²), 2,5-di-tert-butylhydroquinone (0.12 g/m²), and gelatin (0.78 g/m²).

(11) Layer containing a blue-sensitive internal latent image type direct positive silver iodobromide emulsion (halogen composition in the silver halide: 2 mol% of iodine; silver amount: 2.2 g/m²; gelatin: 1.7 g/m²), a fogging agent same as described in Example 2 (0.020 g/m²) and sodium dodecylhydroquinone sulfonate (0.094 g/m²).

(12) Layer containing gelatin (0.94 g/m²).

A piece was cut from the light-sensitive sheet and exposed to light in a camera and processed using a processing solution and a cover sheet same as described in Example 2. Beautiful natural color transferred images having particularly clear red color were obtained.

EXAMPLE 4

A light-sensitive sheet was prepared in the same manner as described in Example 3 except that the compound of the formula below:

[Structure: 4-hydroxy-8-amino-naphthalene with azo linkage to phenyl bearing NO₂ and SO₂CH₃ groups]

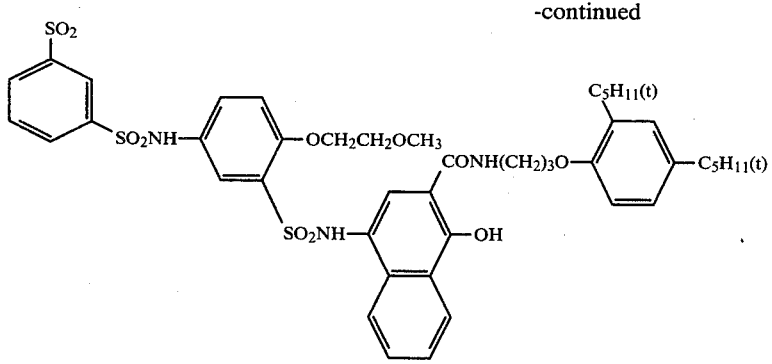

was used in place of the cyan dye releasing redox compound, Compound 12 was used as a magenta dye releasing redox compound and the compound of the formula below:

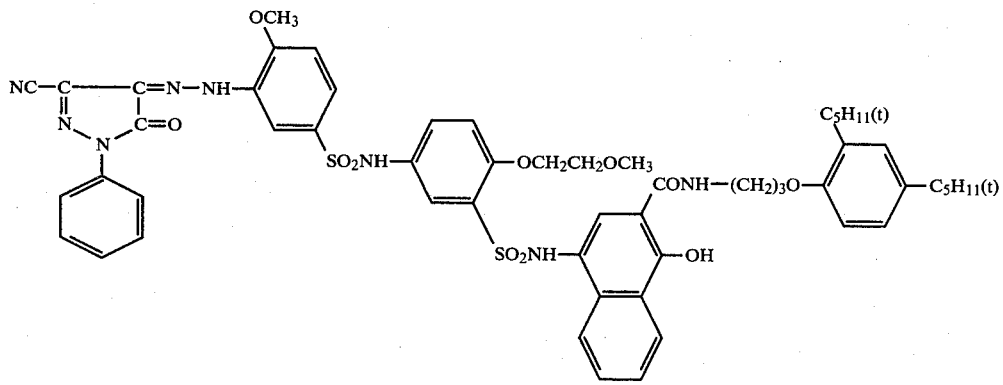

was used in place of the yellow dye releasing redox compound. A piece of the thus obtained light-sensitive sheet was exposed in a camera and processed in the same manner as described in Example 3. Beautiful natural color transferred images were obtained.

While the invention has been described in detail and with reference to specific embodiments thereof, it will be apparent to one skilled in the art that various changes and modifications can be made therein without departing from the spirit and scope thereof.

What is claimed is:

1. A photographic light-sensitive sheet for the color diffusion transfer process which comprises a support having thereon at least one light-sensitive silver halide emulsion layer with at least one of said silver halide emulsion layers having associated therewith a dye image providing material represented by the following general formula:

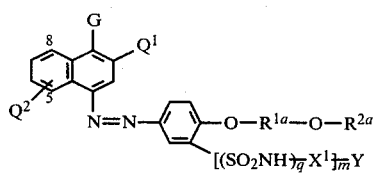

wherein $Q^1$ represents a hydrogen atom, a halogen atom, a sulfamoyl group represented by the formula $-SO_2NR^3R_4$ wherein $R^3$ represents a hydrogen atom or an alkyl group, $R^4$ represents a hydrogen atom, an alkyl group, an aralkyl group or an aryl group, and $R^3$ and $R^4$ may combine directly or through an oxygen atom to form a ring, a group represented by the formula $-SO_2R^5$ wherein $R^5$ represents an alkyl group, or a benzyl group, a carboxy group, a group represented by the formula $-COOR^6$ wherein $R^6$ represents an alkyl group, a phenyl group or a group represented by the formula $-CONR^3R^4$ wherein $R^3$ and $R^4$ each has the same meaning as defined above; $Q^2$, which is positioned at the 5- or the 8-position to the hydroxy group, represents a hydroxy group, a group represented by the formula $-NHCOR^{4a}$ or a group represented by the formula $-NHSO_2R^{4a}$ wherein $R^{4a}$ has the same meaning as $R^4$ defined above except for the absence of a hydrogen atom, $R^{1a}$ represents an alkylene group having 2 or more carbon atoms; $R^{2a}$ represents an alkyl group; Y represents a moiety which releases or provides, as a result of development processing under alkaline conditions, an azo dye having a different diffusibility from that of said dye image-providing material and represents an N-substituted sulfamoyl group; m is 0 or 1; q is 0 or 1; $X^1$ represents a divalent bonding group represented by the formula $-A_1-(L)_n-(A_2)_p-$ wherein $A_1$ and $A_2$ are the same or different and each represents an alkylene group or an arylene group; L represents a divalent group selected from an oxy group, a carbonyl group, a carboxyamido group, a carbamoyl group, a sulfonamido group, a sulfamoyl group, a sulfinyl group and a sulfonyl group, and n and p each represents 0 to 1; and G represents a hydroxyl group, a salt thereof, or a hydrolyzable acyloxy group represented by the formula

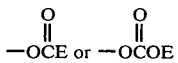

wherein E represents an alkyl group or an aryl group.

2. The photographic light-sensitive material of claim 1, wherein said dye image providing material is represented by the formula:

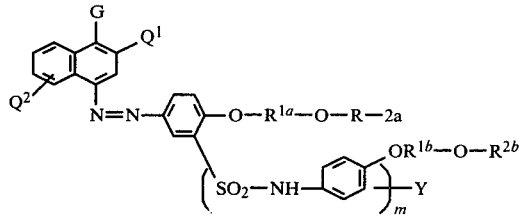

wherein $R^{1b}$ and $R^{2b}$ have the same definition as $R^{1a}$ and $R^{2a}$ and may be the same or different than $R^{1a}$ and $R^{2a}$.

3. The photographic light-sensitive sheet as claimed in claim 2, wherein said alkylene group represented by $R^{1a}$ or $R^{1b}$ is an alkylene group having 2 to 8 carbon atoms.

4. The photographic light-sensitive sheet as claimed in claim 2, wherein said alkyl group represented by $R^{2a}$ or $R^{2b}$ is an alkyl group having 1 to 8 carbon atoms.

5. The photographic light-sensitive sheet as claimed in claim 1, wherein said sulfamoyl group represented by $Q^1$ is a sulfamoyl group represented by the formula $-SO_2NR^3R^4$ wherein $R^3$ is a hydrogen atom or an alkyl group having 1 to 8 carbon atoms; and $R^4$ is a hydrogen atom, an alkyl group having 1 to 8 carbon atoms, an unsubstituted benzyl group, a substituted benzyl group having 7 to 12 carbon atoms, an unsubstituted phenyl group or a substituted phenyl group having 6 to 9 carbon atoms.

6. The photographic light-sensitive sheet as claimed in claim 5, wherein said $R^3$ and $R^4$ each represents a hydrogen atom.

7. The photographic light-sensitive sheet as claimed in claim 5, wherein one of said $R^3$ and $R^4$ represents a hydrogen atom and the other of said $R^3$ and $R^4$ represents an alkyl group having 1 to 4 carbon atoms.

8. The photographic light-sensitive sheet as claimed in claim 1, wherein said Y is a sulfamoyl group represented by the following formula:

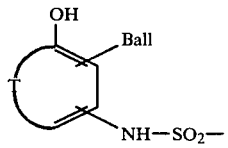

wherein Ball represents a ballast group; T represents the carbon atoms necessary to complete a benzene ring, which may be unsubstituted or substituted, or a naphthalene ring, which may be unsubstituted or substituted; the $NHSO_2-$ group is present at the o- or p-position to the hydroxy group; and when T represents the atoms necessary to complete a naphthalene ring, Ball can be bonded to either of the two rings.

9. The photographic light-sensitive sheet as claimed in claim 8, wherein said ballast group is or contains a hydrophobic residue having 8 to 32 carbon atoms.

10. The photographic light-sensitive sheet as claimed in claim 8, wherein said ballast group is represented by the following formula:

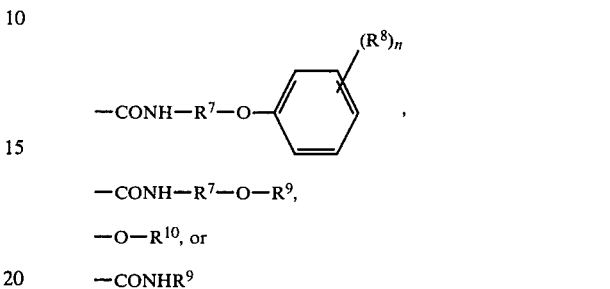

$-CONH-R^7-O-R^9$, $-O-R^{10}$, or $-CONHR^9$ wherein $R^7$ represents an alkylene group having 1 to 10 carbon atoms, $R^8$ represents a hydrogen atom or an alkyl group having 1 to 10 carbon atoms, $R^9$ represents an alkyl group having 4 to 30 carbon atoms and $R^{10}$ represents an alkyl group having 8 to 30 carbon atoms or a substituted alkyl group having 8 or more carbon atoms in which the alkyl moiety has 1 or more carbon atoms.

11. The photographic light-sensitive sheet as claimed in claim 2, wherein $R^{1a}$ and $R^{1b}$ each represents a $-CH_2CH_2-$ group; $R^{2a}$ and $R^{2b}$, which may be the same or different, each represents an alkyl group having 1 to 4 carbon atoms; $Q^1$ represents a hydrogen atom or a sulfamoyl group of the formula $-SO_2NR^3R^4$ wherein $R^3$ and $R^4$, which may be the same or different, each represents an alkyl group having 1 to 4 carbon atoms in the alkyl moiety, and $R^3$ and $R^4$ can combine directly or through an oxygen atom to form a 5- or 6-membered ring; $Q^2$ represents a hydroxy group or an $-NHSO_2R^{4a}$ group substituted at the 5-position, wherein $R^{4a}$ has the same meaning as $R^4$ defined above, except for the absence of a hydrogen atom and Y represents a sulfamoyl group as defined in claim 7.

12. The photographic light-sensitive sheet as claimed in claim 1, wherein $R^{1a}$ is a $-CH_2CH_2-$ group; $R^{2a}$ represents an alkyl group having 1 to 4 carbon atoms; $Q^1$ and $Q^2$ each has the same meaning as defined in claim 10; Y represents an o-hydroxyphenylsulfamoyl group having an alkyl group at the meta position to the hydroxy group in addition to a ballast group; and m is 0.

13. The photographic light-sensitive sheet as claimed in claim 1, wherein said Y is an N-substituted sulfamoyl group wherein the substituents in an o- or p-hydroxyaryl group having a ballast group bonded thereto.

14. The photographic light-sensitive sheet as claimed in claim 1, wherein said G group is a hydroxy group.

15. The photographic light-sensitive sheet as claimed in claim 1, wherein said dye image-providing material is a dye-releasing redox compound.

* * * * *